United States Patent [19]
Bellahsène et al.

[11] Patent Number: 5,850,496
[45] Date of Patent: Dec. 15, 1998

[54] ENDOSCOPE WITH INTEGRATED, SELF-REGULATING LIGHT SOURCE

[75] Inventors: Bader-Eddine Bellahsène, Cuppertino; Albert R. Luna, San Jose, both of Calif.

[73] Assignee: Stryker Corporation, Kalamazoo, Mich.

[21] Appl. No.: 886,955

[22] Filed: Jul. 2, 1997

Related U.S. Application Data

[60] Provisional application No. 60/024,198 Aug. 26, 1996.

[51] Int. Cl.$^6$ ........................................ G02B 6/06
[52] U.S. Cl. ..................... 385/117; 385/118; 385/101; 250/227.11
[58] Field of Search ................................. 385/117, 118, 385/119, 53, 55, 101; 250/227.11, 554; 604/51, 118, 169

[56] References Cited

U.S. PATENT DOCUMENTS

| | | | |
|---|---|---|---|
| 4,601,284 | 7/1986 | Arakawa et al. | 128/6 |
| 4,623,788 | 11/1986 | Kern et al. | 250/227.11 |
| 5,115,126 | 5/1992 | Ams et al. | 250/227.11 |

FOREIGN PATENT DOCUMENTS

| | | |
|---|---|---|
| 0 027 608 | 4/1981 | European Pat. Off. . |
| 0 049 447 | 4/1982 | European Pat. Off. . |
| 0 416 408 A2 | 3/1991 | European Pat. Off. . |
| 56-065107 | 6/1981 | Japan . |
| 57-044116 | 3/1982 | Japan . |

OTHER PUBLICATIONS

Stryker Endoscopy Blueprint of Light Cable Port, Oct., 1996, 3 pages.

*Primary Examiner*—Phan T.H. Palmer
*Attorney, Agent, or Firm*—Flynn, Thiel, Boutell & Tanis, P.C.

[57] ABSTRACT

An endoscope system (20) comprising an endoscope (22) with light source (28). A light generated by the light source is supplied to the endoscope by a fiber optic cable (46). The cable in addition to including an optically transmissive core (50), includes two conductors (62) that are not in direct electrical contact with each other. Contacts (70, 71) in a plug attached to one end of the cable attach the conductors to circuitry internal to the light source. Contacts (80, 84) in a plug at the opposed end of the cable also provide at the opposed end of the cable. When the cable is attached to the endoscope, contacts (80, 84) are shorted together so as to complete the circuit established therebetween. This circuit completion state is monitor by the light source. When the cable is disconnected from the endoscope this connection is broken. This disconnect state is recognized by the light source as an endoscope-disconnected condition. When this condition is recognized, the light source automatically places itself in a standby mode reducing the amount of emitted light energy, thus minimizing heating of the light cable, distal, scope-end, tip.

22 Claims, 20 Drawing Sheets

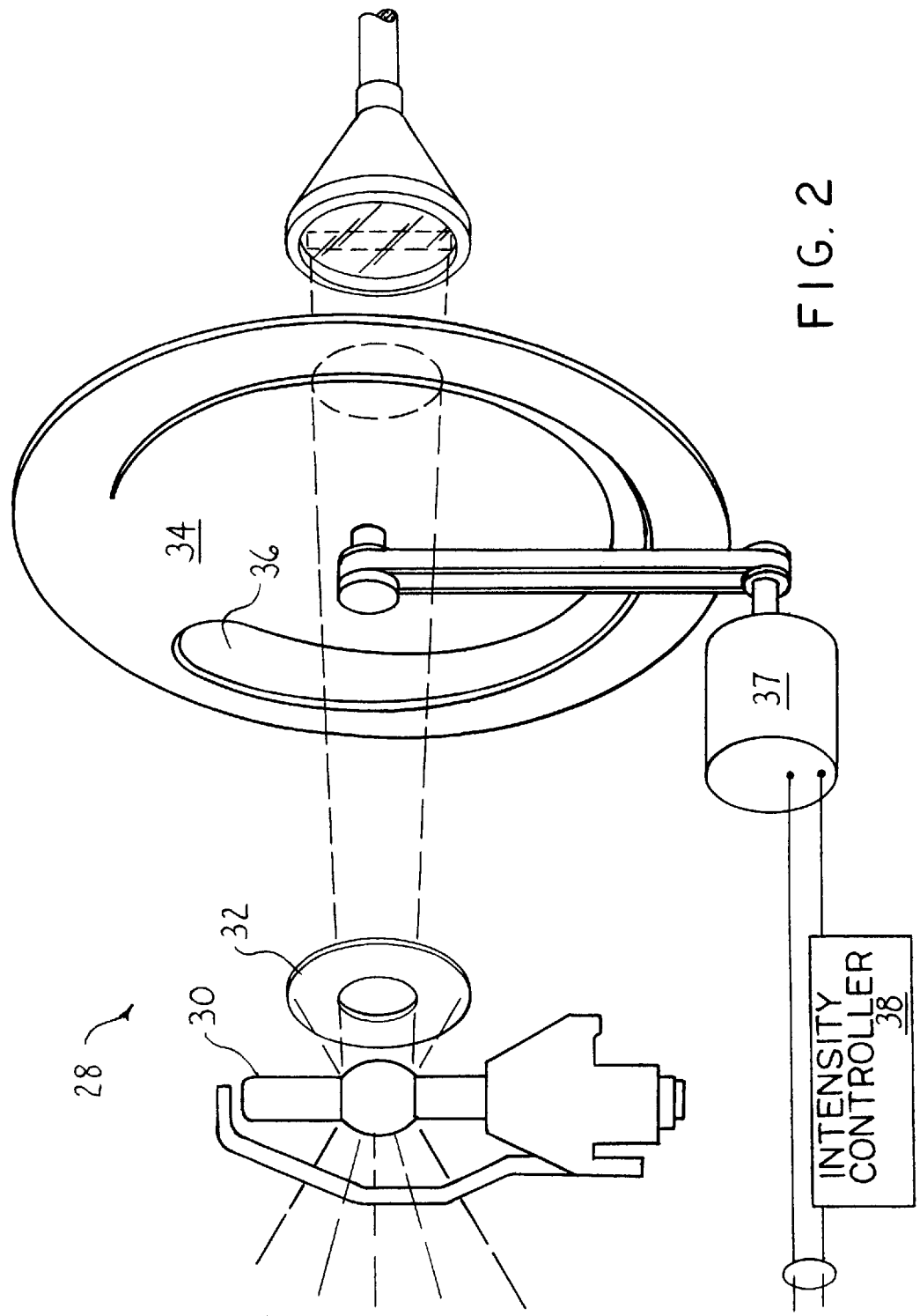

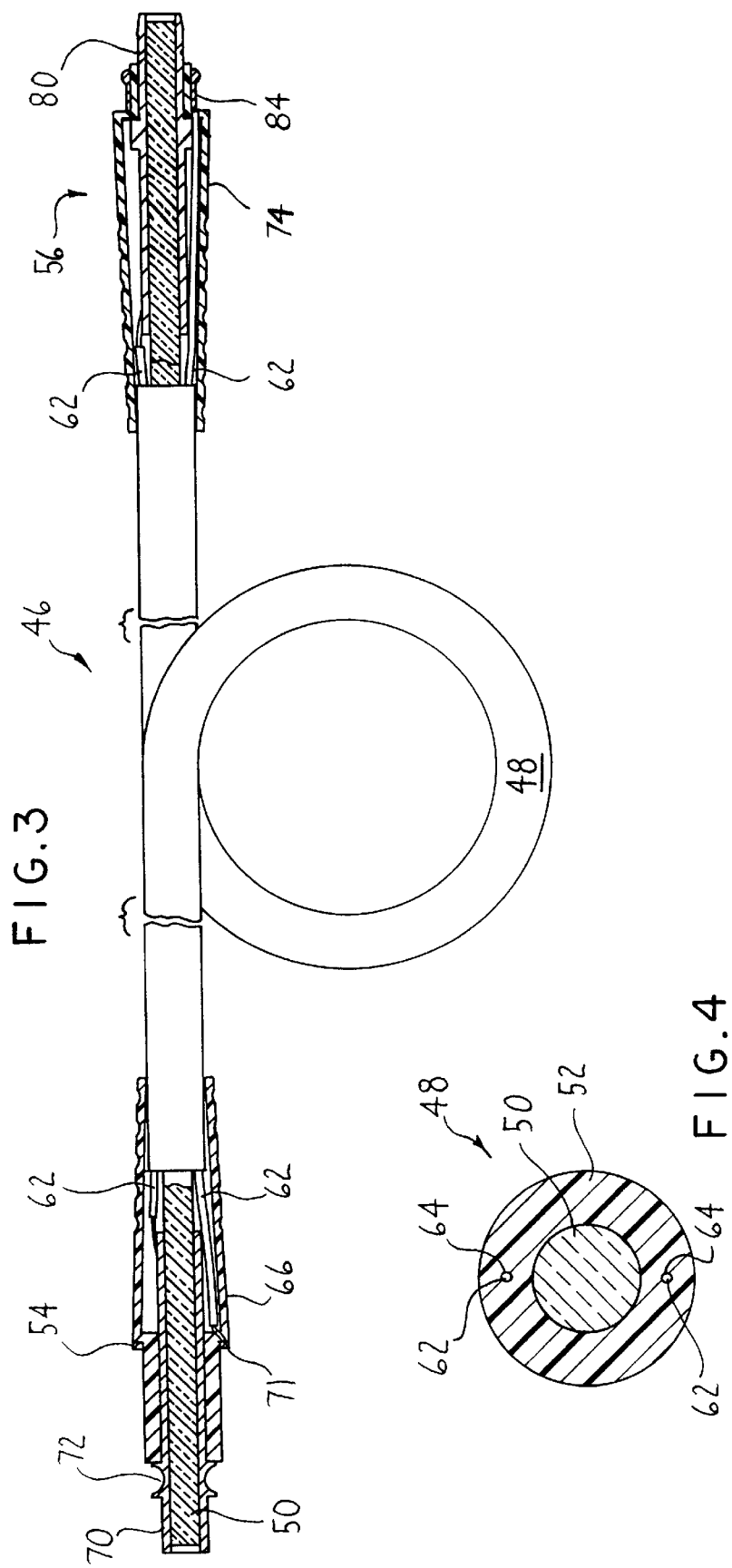

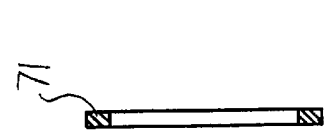
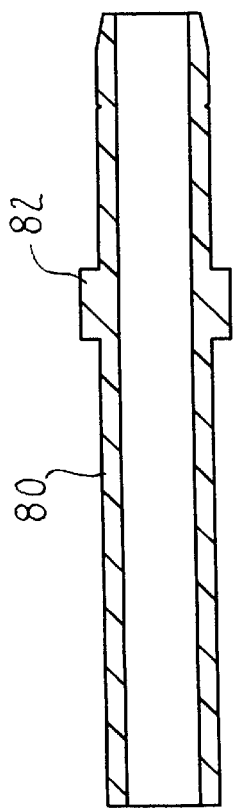
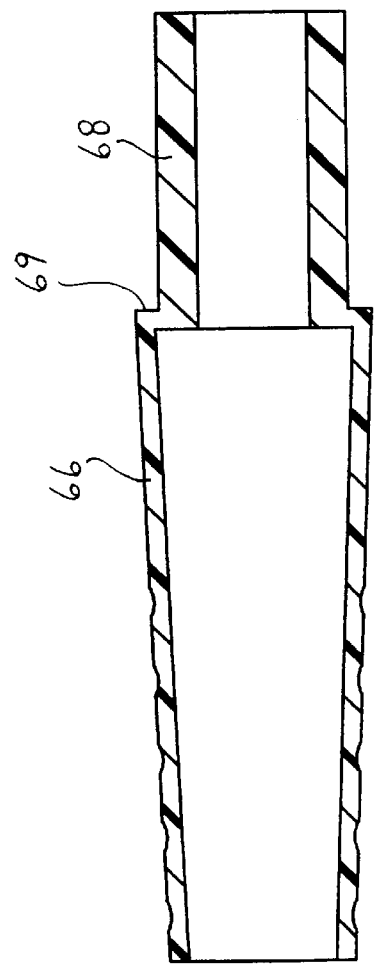

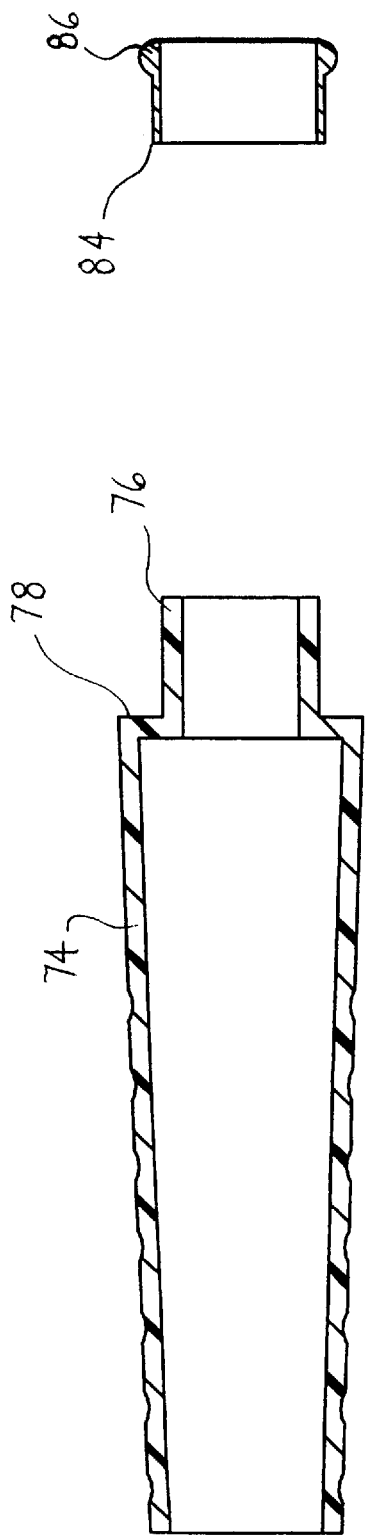
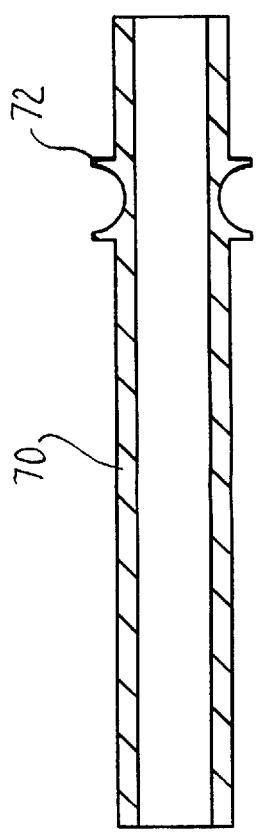

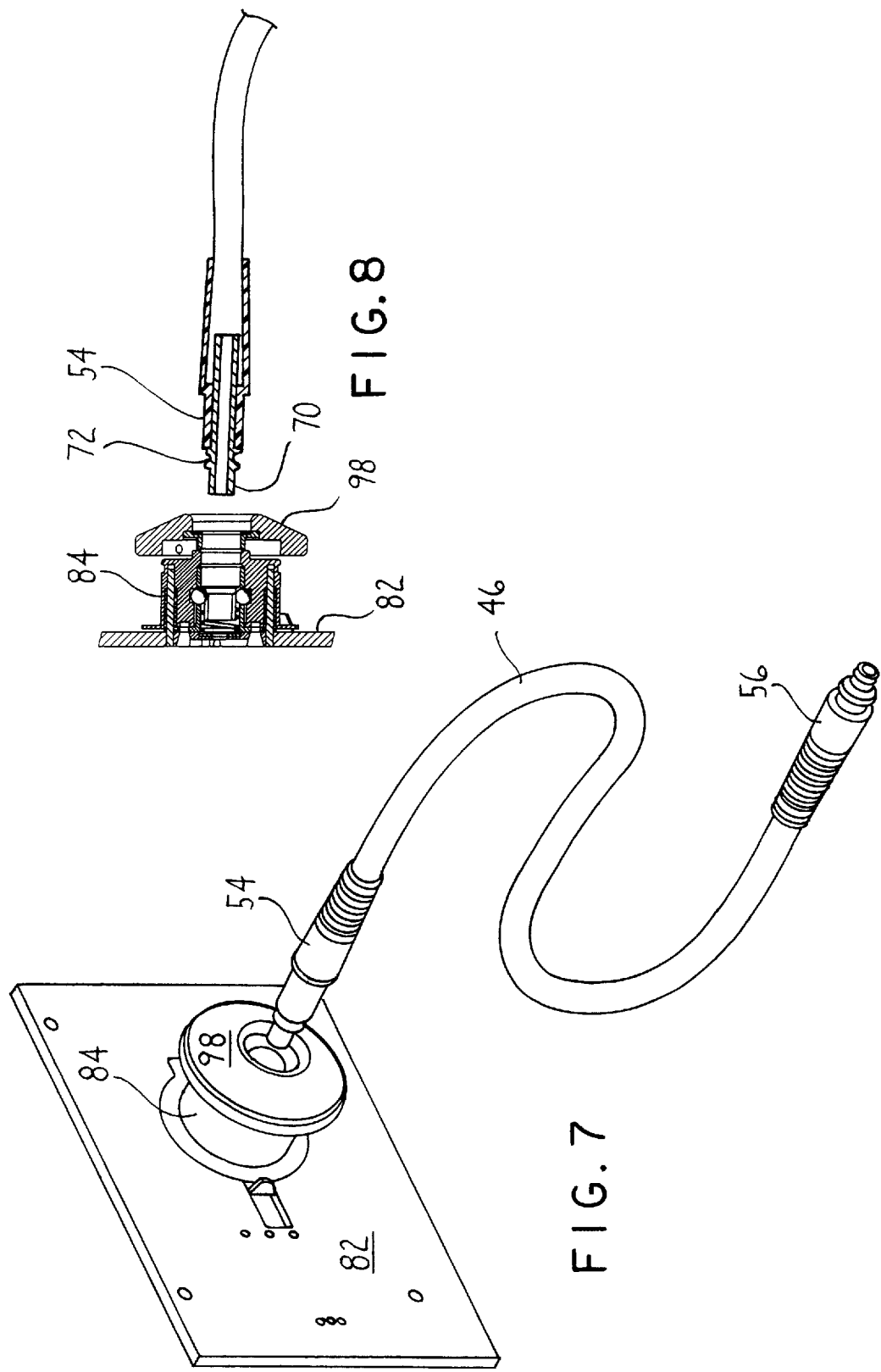

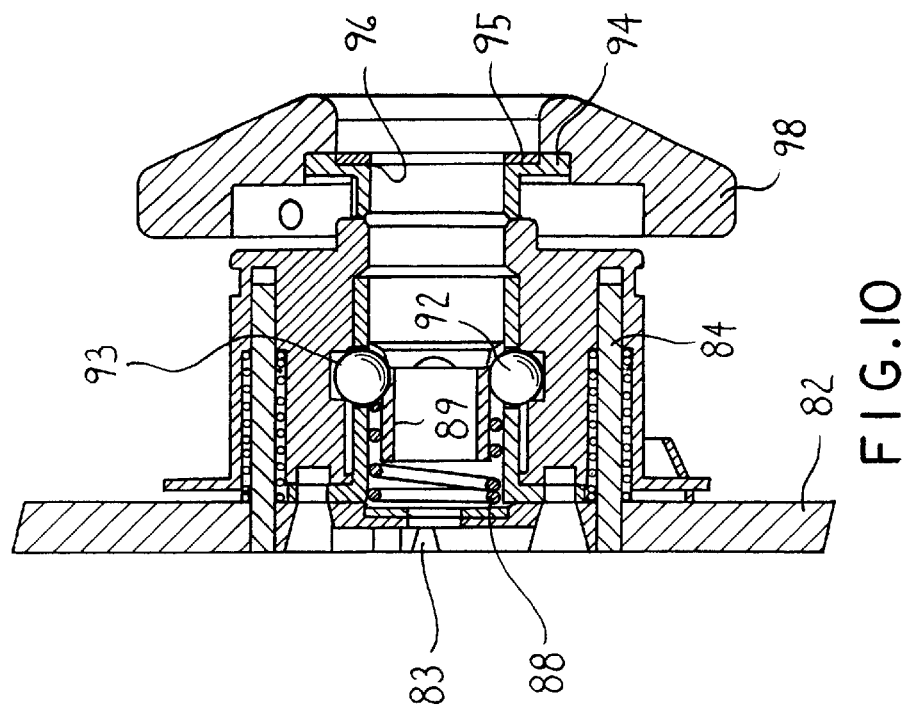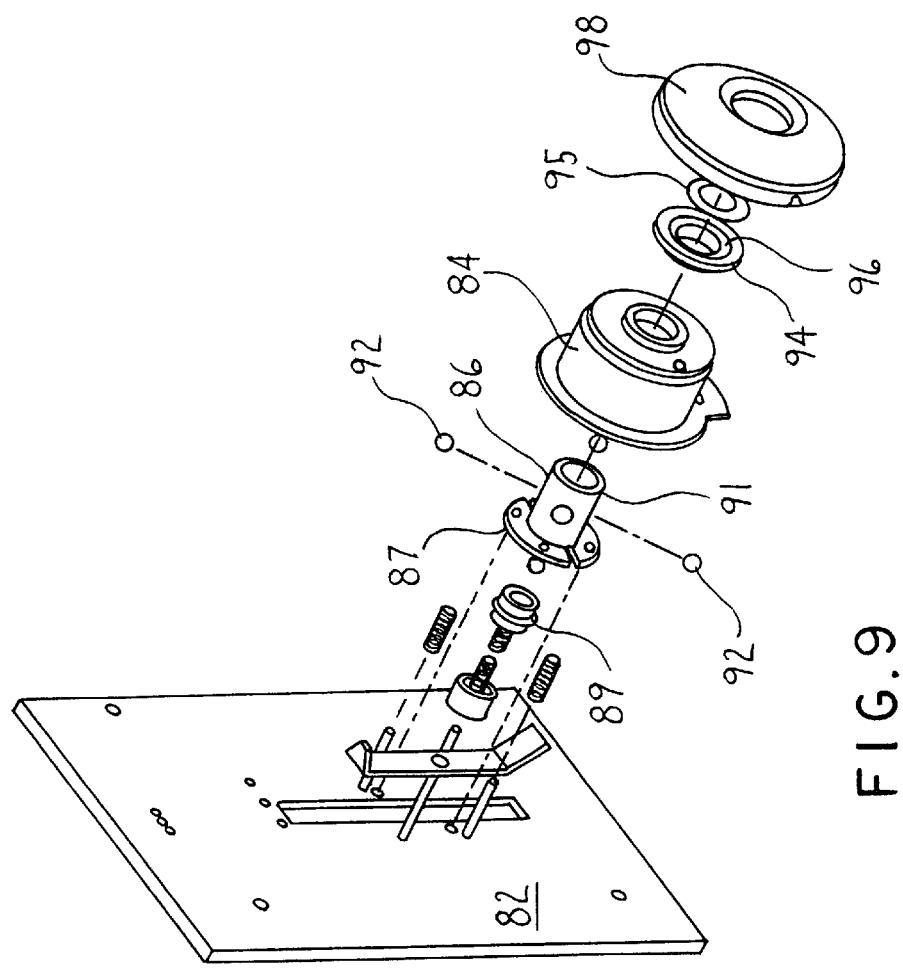

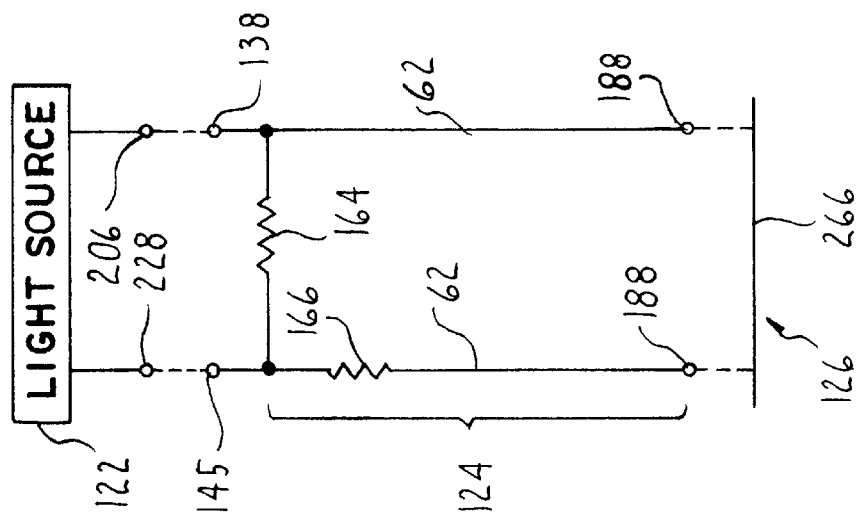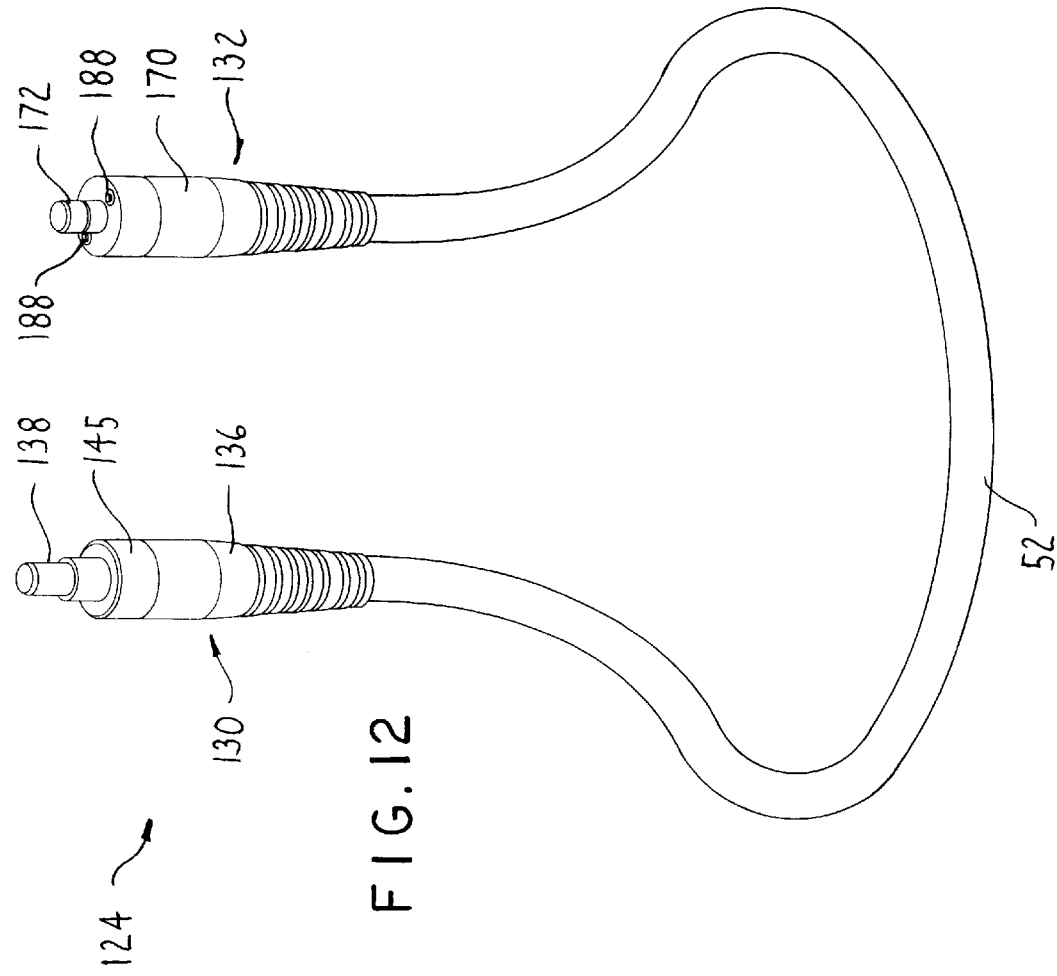

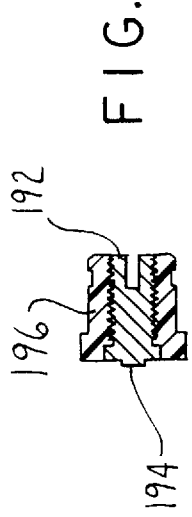
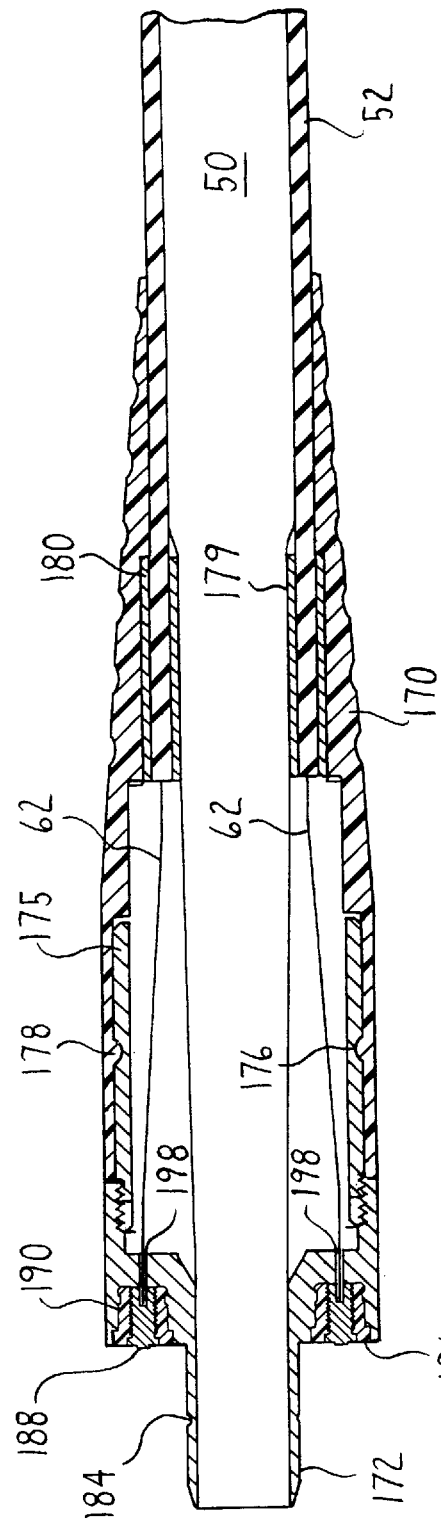
FIG. 14A
FIG. 14

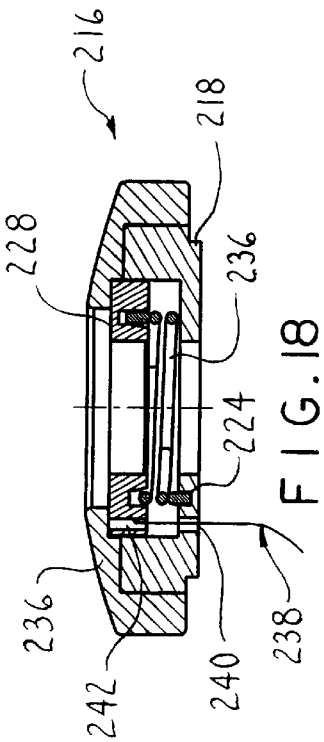
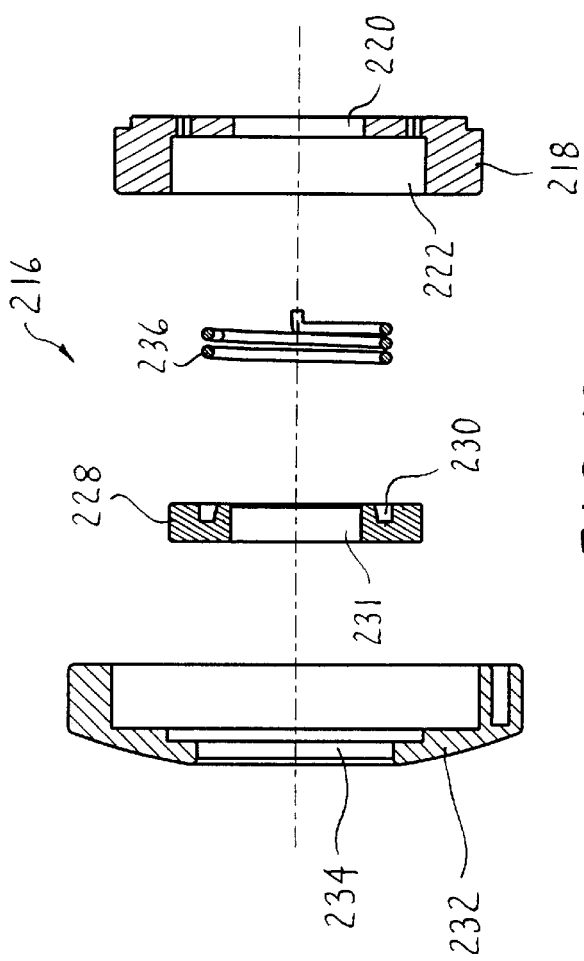

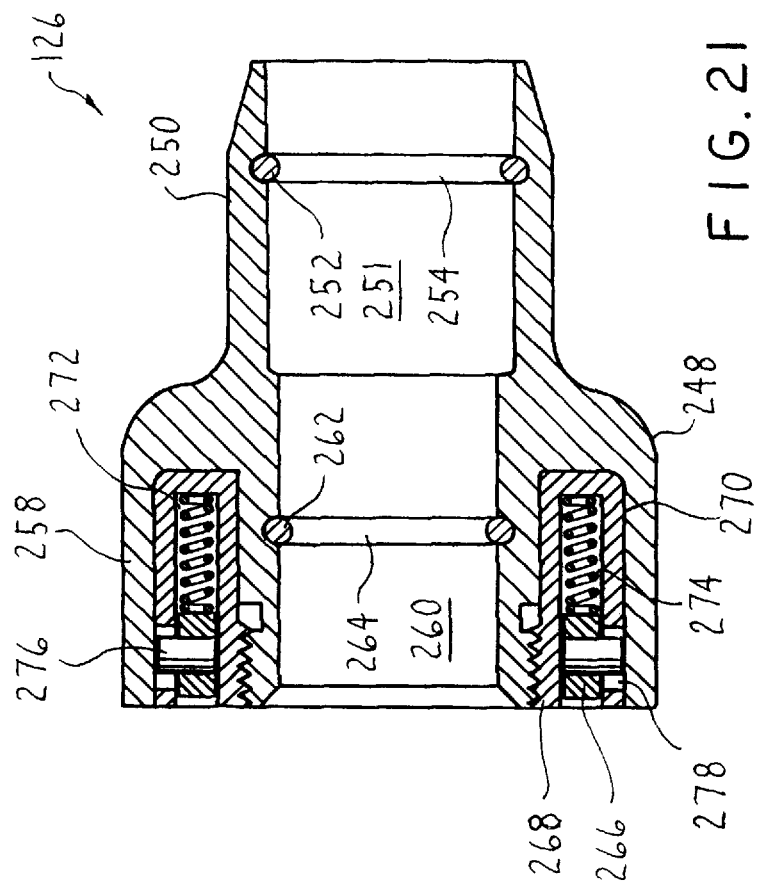

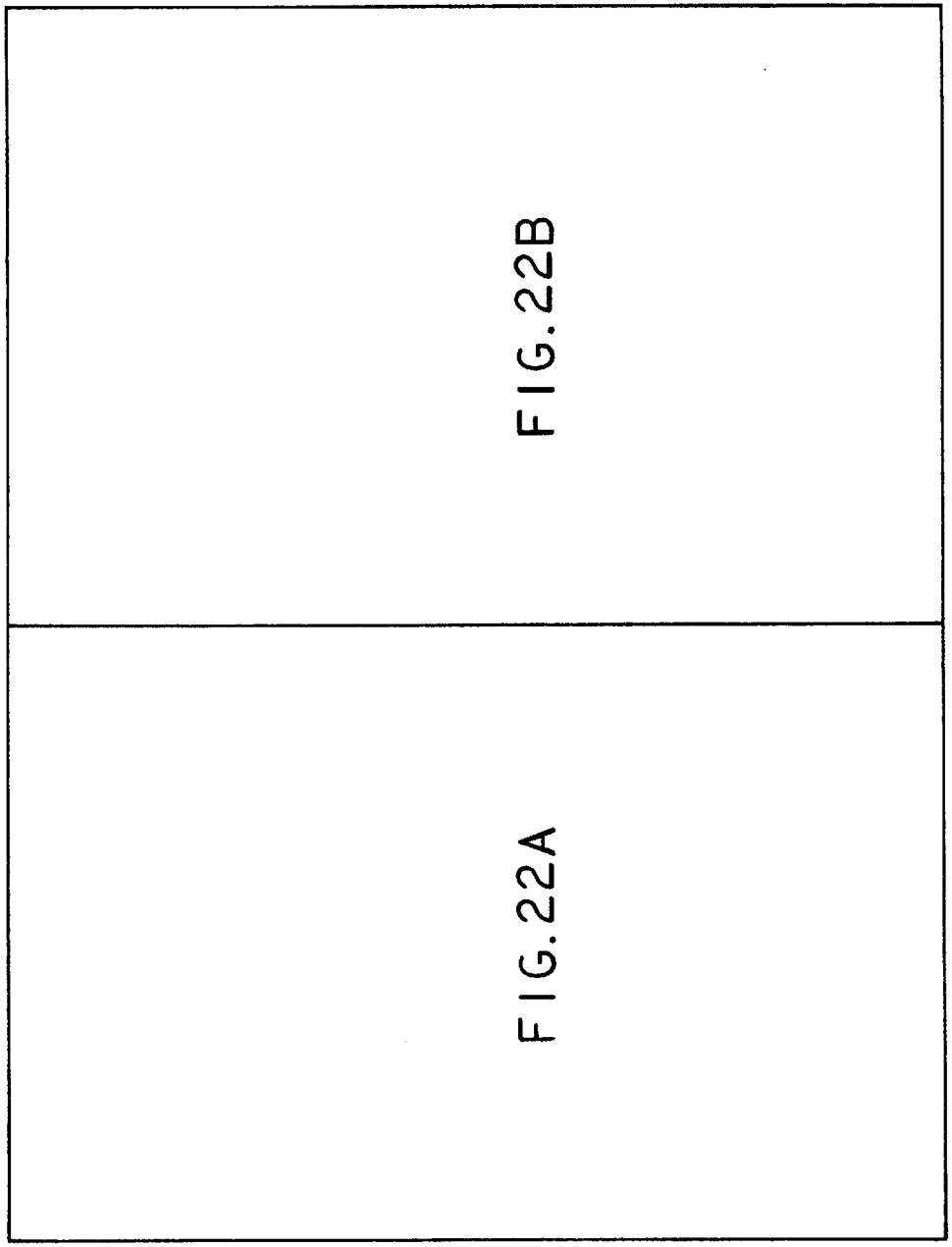

ENDOSCOPE WITH INTEGRATED, SELF-REGULATING LIGHT SOURCE

RELATIONSHIP TO EARLIER FILED APPLICATION

This application claims priorrity from U.S. provisional patent application Ser. No. 60/024,198, filed Aug. 26, 1996.

FIELD OF THE INVENTION

This invention relates generally to endoscopes designed to facilitate minimally invasive surgery and, more particularly, to an endoscope with an integrated light source that self-regulates the intensity of the light emitted by the light source.

BACKGROUND OF THE INVENTION

An endoscope is a surgical tool designed to be placed inside a body in order to provide a view of the portion of the body in which it is inserted. In endoscopic surgery, an endoscope is placed in a body at the location at which it is necessary to perform a surgical procedure. Other surgical instruments are placed in the body at the surgical site. The surgeon views the surgical site through the endoscope in order manipulate the other surgical instruments to perform the desired surgical procedure. The development of endoscopes and their companion surgical instruments has made it possible to perform minimally invasive surgery that eliminates the need to make a large incision to gain access to the surgical site. Instead, during endoscopic surgery, small openings, called portals, are formed. One advantage of performing endoscopic surgery is that since the portions of the body that are cut are reduced, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

The ability to perform endoscopic surgery is enhanced by the availability of light sources designed to illuminate the surgical site inside the patient. A typical light source includes a light-emitting bulb that is located outside of the patient in a control console. A fiber optic cable extends between the control console and the endoscope. The cable has a proximal end that is adapted to receive the light emitted by the bulb and a distal end that is coupled to a complementary light post integral with the endoscope. (Hereinafter it shall be understood that "proximal" means towards the light source and "distal" means towards the endoscope.) When the light source is energized, the light emitted by the bulb is transmitted through the cable to the endoscope. A set of optical fibers in the endoscope transmit the light to the surgical site. The emitted light illuminates the surgical site so as to make it easier for surgical personnel to observe the site.

While current light sources have facilitated the advancement of endoscopic surgery, they are not without disadvantages. One particular disadvantage relates to the fact that, in order to illuminate a surgical site, the light source for an endoscopic is required to transmit a large amount of light energy. For example, some of these light sources include light emitting bulbs that is supplied with 250 Watts, have luminous intensity of approximately 2,500 candela, and an average luminance of 40,000 $cd/cm^2$. Problems arise with these light sources because, during endoscopic surgery, it may be necessary to switch the endoscope that is used on a patient. A change of endoscope may be necessary if, during the surgical procedure, a different field of view of the surgical site is desired; such change in perspective can sometimes only be obtained by switching endoscopes. During this switch of the endoscopes, the distal end of the fiber optical cable is disconnected from the first endoscope and coupled to the second endoscope. Prior to the fiber optic cable being attached to the second endoscope, it is often momentarily placed on a surgical drape. A problem can occur because the light energy emitted by the fiber optic cable can rapidly warm the surface on which the distal end of the cable is placed. If the surface is cloth or paper, such as a surgical drape, there is a potential that this energy may singe the drape. If the fiber optic cable is inadvertently left on the drape for an extended period of time, the heat generated could potentially cause the drape to either burn or ignite.

SUMMARY OF THE INVENTION

This invention relates generally to an improved endoscope with integrated light source designed to reduce the extent to which the light emitted by the light source has the potential for being a thermal hazard in a surgical suite.

BRIEF DESCRIPTION OF THE DRAWINGS

This invention is pointed out with particularity in the claims. The above and further advantages of this invention may be better understood by reference to the following description taken in conjunction with the accompanying drawings, in which:

FIG. 2 is a diagrammatic illustration of light bulb and companion intensity controller internal to the light source of this invention;

FIG. 3 is a partial plan view of the fiber optic cable with the plugs integral therewith depicted in cross-section;

FIG. 4 is a cross sectional view through the center of the fiber optic cable;

FIGS. 5A, 5B and 5C are cross sectional views of components forming the proximal-end plug of the fiber optic cable;

FIGS. 6A, 6B and 6C are cross sectional views of components forming the distal end plug of the fiber optic cable;

FIG. 7 is a plan view illustrating how the fiber optic cable is coupled to the socket (light cable port) integral with the light source;

FIG. 8 is a cross sectional view illustrating how the fiber optic cable is coupled to the socket integral with the light source;

FIG. 9 is an exploded view of the components forming the socket integral with the light source;

FIG. 10 is a cross sectional view of the socket integral with the light source;

FIG. 12 is a perspective view of the light cable employed in the system of FIG. 11;

FIG. 14 is a cross-sectional view of the scope-end plug of the cable of FIG. 12;

FIG. 14A is a detailed cross-sectional view of the electrical contact depicted in FIG. 14;

FIG. 18 is an exploded cross-section view of the knob assembly integral with the light source in which the cable is inserted;

FIG. 19 is a cross-sectional view of the knob assembly of FIG. 18;

FIG. 21 is a cross-sectional view of the adaptor of FIG. 20;

FIG. 22 is an assembly diagram depicting how FIG. 23 is a schematic drawing of the conductors and other electrical components integral with the light cable and a representation of how the light cable is electrically connected to the light source and adapter.

DETAILED DESCRIPTION

Figure 1:
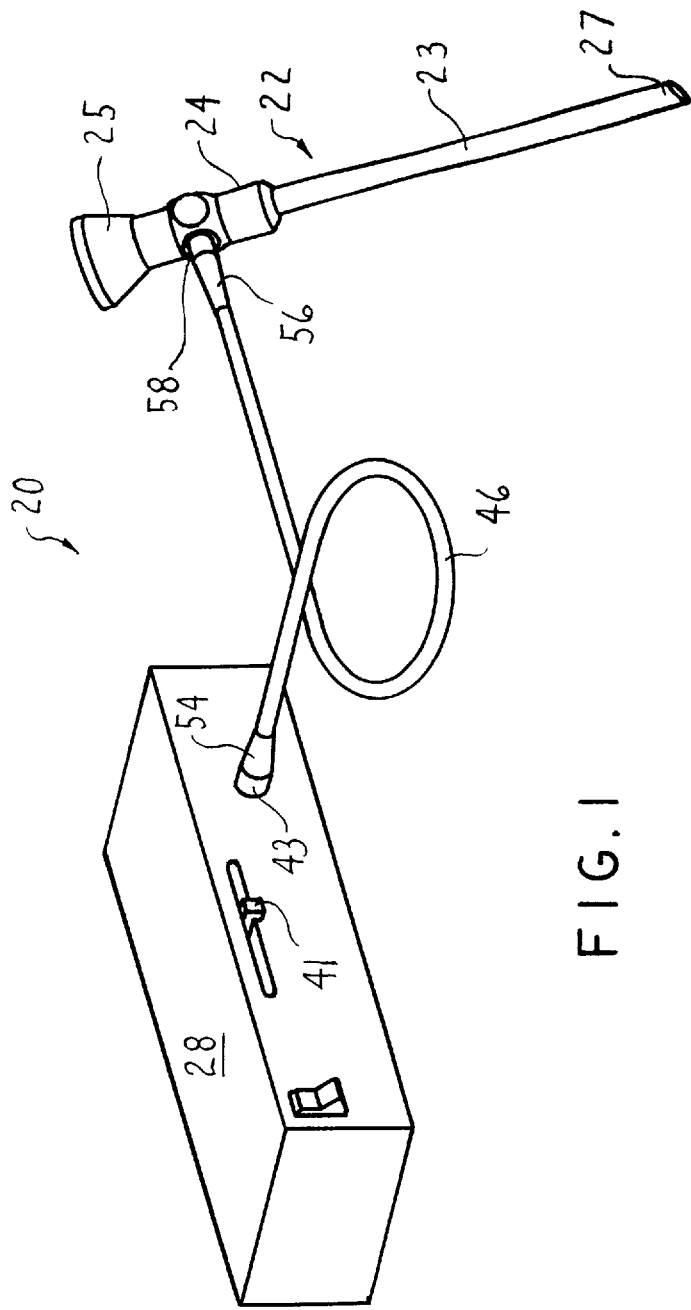
FIG. 1 is block diagram of the main features of the endoscope with integrated light source of this invention.

FIG. 1 illustrates the basic features of the endoscopic system 20 of this invention. The endoscopic system 20 includes an endoscope 22. The endoscope has an elongated hollow shaft 23 with a distal end 27 that is positioned inside the body of the patient. A window, not illustrated covers the distal end of the shaft 23. The shaft 23 also has a proximal end 24 that remains outside of the patient. An eyepiece 25 is fitted over the proximal end 24 to provide a viewing port through which the surgeon views the surgical field. Optical focusing elements, not illustrated, in the shaft 23 serve to enhance the visible field of view. The eyepieces 25 of many endoscopes are designed to hold a television camera. These cameras provide surgical personnel with a view of the surgical site on complementary monitors to which they are connected.

Endoscopic system 20 includes a light source 28 for illuminating the surgical site. As seen by reference to FIG. 2, light source 28 includes a bulb 30 for emitting light that is used to illuminate the surgical site at which the endoscope 22 is directed. In one preferred version of this invention, bulb 30 is a bulb sold under the trademark HALOMITE as Bulb HTI 250W/SE. The light emitted by bulb 30 is directed through a focusing ring 32. The light emitted by bulb 30 is directed from ring 32 towards a circular shutter 34 that is rotatingly mounted in the light source 26. Shutter 34 is formed to define a curved aperture 36 immediately inside the perimeter of the shutter that has a variable cross sectional width. The light emitted by bulb 30 is directed towards a fixed location that is offset from the center of shutter 34. By the selective positioning of the aperture 36 relative to the point at which the light is directed, light source 28 controls the intensity of the light emitted therefrom. By selectively positioning shutter 34, a maximum of 100% of the light emitted by bulb 30 to just 5 to 20% of the light emitted can be transmitted from the light source 28. The light emitted by light source 28 is emitted through a socket 43 (FIG. 1).

Shutter 34 is selectively rotated to set the position of aperture 36 by a stepper motor 37. An intensity controller 38 selectively actuates stepper motor 37 in response to user-entered and automatic command signals in order to regulate the amount of light emitted by light source 28. The intensity controller 38 can be controlled by one of two inputs. The light emitted can be controlled manually by the displacement of slide switch 41, e.g. a potentiometer, located on the face of the light source 28.

Alternatively, it is contemplated that the intensity controller 38 may regulate the position of the shutter 34 automatically based on externally generated command signals. These command signals are asserted by a control unit, (not illustrated) integral with the television camera that may be mounted to the eyepiece 25 of the endoscope 22. More particularly, the amplitude of the video signal received from the television camera is used as a feedback signal for controlling the intensity of the light emitted by the light source 28. In this manner, the brightness of the image generated by the television camera inferentially controls the intensity of the light emitted by the light source.

The intensity controller 38 further has a circuit for placing the light source 28 in what is referred to as a standby mode. When the light source 28 is in the standby mode, the signal measured as result of the position of the slide switch 41 or the external command signal is not used to establish the position of the shutter 34. Instead, when the light source 28 is in the stand-by state, intensity controller 38 automatically actuates stepper motor 37 to move the shutter 34 so that only a minimal amount of light is emitted from the light source 28.

The light emitted by light source 28 is transmitted to the endoscope 22 over a fiber optic cable 46 coupled to socket 43. Fiber optic cable 46, now described by initial reference to FIGS. 3 and 4, includes a cable body 48 in which there is an elongated core 50 formed out of optically transmissive material. A protective, insulating tubing 52 is disposed around the core 50. In some versions of the invention, tubing 52 is at least partially transparent in order to provide a quick visual indication of the on/off state of the light source and the intensity of the light emitted thereby. One end of fiber optic cable 46 is fitted with a proximal end plug 54 designed to be coupled into light source socket 43. The opposed end of cable body 48 of fiber optic cable 46 is fitted with a distal end plug 56. Distal end plug 56 is designed to be fitted into a complementary light post 58 integral with the shaft 23 of the endoscope 22 adjacent eyepiece 25 (FIG. 1). Fiber optical cables internal to the shaft 23 forward the light to the distal end of the shaft, cables not illustrated.

Fiber optic cable 46 further includes two insulated electrical conductors 62 over which a signal is applied to provide light source 28 with an indication of whether or not the cable 46 is attached to an endoscope 22. Conductors 62 each of which is insulated, extend the length of cable body 48. In the depicted version of the invention, each conductor 62 is contained in an individual conduit 64 formed in the tubing 52 of the cable.

As seen by reference to FIGS. 3, 5A, 5B and 5C proximal-end plug 54 includes a plastic, insulating outer body 66 that is fitted over the adjacent end of cable body 48. The outer body 66 of proximal-end plug 54 includes a sleeve-like head 68 that projects beyond cable body 48. A small annular step 69 defines the separation of the main portion of the plug outer body 66 from head 68. A metallic head sleeve 70 is fitted inside head 68 of outer body 66 so as to extend outside of head 68. In the illustrated version of the invention, head sleeve 70 is formed with a ring 72 that extends around the sleeve 70 adjacent the forward end of the head 68 of plug outer body 66. Ring 72 is formed with a concave profile designed to facilitate the seating therein of conventional spring loaded balls associated with light source socket 43. The proximal end of cable core 50 appears at the open end of head sleeve 70.

A first one of the conductors 62 of fiber optical cable 46 is electrically connected to the end portion of head sleeve 70 disposed in the main portion of the outer body 66 of the plug 54. The second conductor 62 extends through a small opening in the step portion 69 of plug outer body 66. The second conductor 62 electrically attached to a metallic, conductive, washer-like ring 71 that is seated against the outer surface of step 69.

As seen by reference to FIGS. 3, 6A, 6B and 6C, distal-end plug 56 includes a plastic, insulating outer body 74 that is fitted over the adjacent end of cable body 48. The outer body 74 of distal-end plug 56 includes a sleeve-like head 76 that projects forward of both cable body 48 and the main portion of outer body 74. A small annual step 78 defines the separation of the main portion of the plug outer body 74 from head 76. A metallic, conductive head sleeve 80 is fitted inside head 68 of outer body 48 so as to extend outside of head 76. In the illustrated version of the invention, head sleeve 80 is formed with a collar 82 that has a rectangular cross sectional profile. Head sleeve 80 is seated in the outer body 74 of plug 56 so that the leading surface of collar 82 bears against the inside surface of step 78. The most forward end of cable core 52 appears at the open end of head sleeve 80.

A sleeve-like coupling ring 84 formed of a conductive metal is fitted around the outside of the head 76 of the outer body 74 of plug 56. A lip 86 with an outwardly directed, convex cross sectional profile is formed integrally with the forward end of coupling ring 84. The coupling ring 84 is designed to engage a complementary locking tongue associated with endoscope 22. A first one of the conductors 62 of fiber optical cable 42 is electrically connected to an end portion of head sleeve 80 disposed in the main portion of the outer body 74 of the plug 56. The second conductor 62 extends through a small opening in the step portion 78 of plug outer body 74. The second conductor 62 is electrically attached to coupling ring 84.

Socket 43 of the light source 28 is now described by reference to FIGS. 7–10. Socket 43 includes an adapter plate 82 fitted over the front face of the light source 28. Adapter plate 82 is formed with an opening 83 through which the light generated by bulb 30 and passed through the shutter 34 is emitted. A cylindrical knob body 84 is fitted over adapter plate 82 so as to be centered over opening 83. Knob body 84 is formed with a center bore 85 that extends axially therethrough. A tubular base 86 is fitted inside the bore 85 of knob body 84. Base 86 is further provided with a circumferential flange 87 around the proximal end thereof that is secured against adapter plate 82. A spring 88 is located in the bottom of the base. A tube like spring hat 89 is located above spring 88. Base 86 is further formed with four circular openings 91 spaced 90 degrees apart from each other that are located adjacent the forward edge of the spring hat 89. A ball bearing 92 is seated in each one of the openings 91. Knob body 84 is formed with a rectangular groove 93 for receiving the outer portions of bearings 92.

A plastic seating ring 94 is located around the exposed open end of bore 85 of knob body 84. A metal, conductive contact washer 95 is fitted in the top of seating ring 94. More particularly, washer 95 is seated in a groove 96 formed in the outermost surface of seating ring 94. A circular knob adapter 98 functions as the outer member of socket 43. Knob adapter 98 has a center opening 102 designed to accommodate the head portion of proximal-end plug 54.

When proximal-end plug 54 is seated in socket 43, ball bearings 92 seat in the concave space defined by ring 72 of head sleeve 70 so as to lock the plug in the socket. When proximal-end plug 54 is so positioned, the metal surface of head sleeve 70 is in contact with the adjacent inside metal surface of spring hat 89. Conductive ring 71 of plug 54 is in contact with conductive washer 95 of socket 43. Wires, not illustrated, extending from spring hat 89 and conductive washer 95 provide an electrical connection from these members to intensity controller 38.

A similar socket-like assembly is disposed on the light post 58 of endoscope 22. In some preferred versions of the invention, this assembly is actually an adapter arranged to be removably secured to the light post 58. More particularly, this socket or adapter includes a conductive, tube-like member against which the outer surface of head sleeve 80 abuts. There is also one or more conductive locking members designed to be positioned against the lip 86 of coupling ring 84 in order to hold distal-end plug 56 to the endoscope 22. A conductor extends between the member against which head sleeve 80 abuts and the lock member(s) that engage coupling ring 84.

The endoscopic system 20 of this invention is used in the manner similar to which conventional endoscopic systems are used. The light generated by the source 28 is supplied to the endoscope 22 through the fiber optic cable 46. As long as the cable 46 remains attached to the light source 28 and the distal plug 56 is plugged into the adaptor fitted to the light post 58 the endoscope 22 a closed circuit is established across conductors 62 integral with the cable 46. The monitoring circuit internal to the intensity controller 38 is preferably an electronic circuit which detects the voltage across conductors 62 as an indication that the cable 46 is plugged into the endoscope. Consequently, the monitoring circuit asserts a signal to the intensity controller that releases the intensity controller from the stand-by state. This allows the controller 38 to set the intensity of the emitted light up from the minimal setting based on either manual controls or the signals from the television system.

If, however, the distal plug 56 of the cable 46 is disconnected from the endoscope 22, the connection across conductors 62 is broken. The monitoring circuit detects this open circuit state as an indication that the fiber optical cable 46 has been disconnected from the endoscope 22. Consequently, the monitoring circuit asserts a signal to intensity controller 38 that causes the intensity controller to go into the stand-by state. The intensity controller then automatically actuates stepper motor 37 so as to cause the resetting of the shutter 34 to a low light emission state. As a result of this resetting of the shutter, only a relatively small amount of light is emitted by the light source 28.

When distal plug 56 of cable 46 is plugged back into an endoscope, the connection across conductors 62 is reestablished. The complementary monitoring circuit reasserts the signal to intensity controller 38 indicating the establishment of the endoscope connection. Once this signal is again received, the intensity controller is released from the stand-by state. In some versions of the invention, the light source is only released from the stand-by state by the subsequent manual actuation of a stand-by release switch on the face of the light source. Once the intensity controller is released from the stand-by state, the intensity controller again actuates the stepper motor 37 so as to return the shutter 34 to its previous aperture position. The return of shutter 34 to its initial position causes the light source to emit the same amount of light as it previously emitted.

The endoscopic system 20 of this invention provides a convenient means of providing light to a surgical site at which an endoscope is placed. An advantage of this system is that it prevents the light source 28 integral with the system from emitting large amounts of light unless the light is being applied to the complementary endoscope 22. Thus, if in the course of surgery, the light source is disconnected from the endoscope 22, the light source, without any command required by surgical personnel, will automatically reduce the amount of light it sends through the associated fiber optic cable 46. Consequently, during this disconnect period, the distal plug 56 of the fiber optic cable can be placed on a surface without risk that the plug (or more precisely the light cable distal tip) may singe or burn the surface. Moreover, since only a minimal amount of light energy is being emitted by the fiber optic cable when so disconnected, the possibility that surgical personnel handling the plug will inadvertently burn their hands is likewise reduced.

Moreover, once the fiber optical cable 46 is reconnected to an endoscope, the intensity controller 38 automatically adjusts the shutter 34 so that the light source will again emit the same amount of light as it did before it was disconnected. Thus, the endoscopic system of this invention provides a means for applying light to the surgical site at which it is used and that prevents light from being emitted when it is not needed. This eliminates the possibility that unneeded light at the distal end plug can be the source of potentially damagecausing thermal energy.

Figure 11:
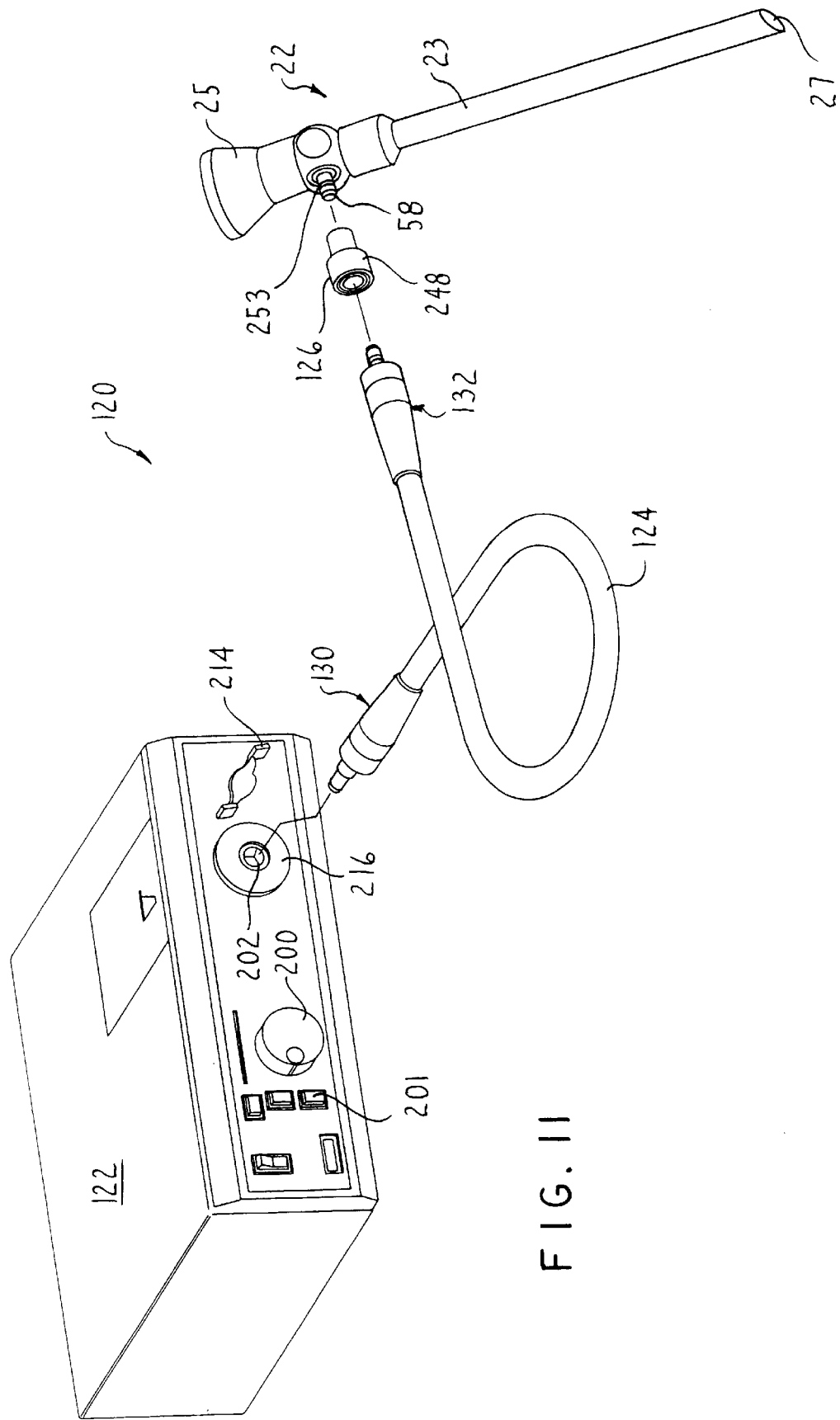
FIG. 11 depicts an alternative endoscope with integrated light source system of this invention.

FIG. 11 illustrates still another endoscope system 120 of this invention. System 120 includes the previously described endoscope 22. In this Figure, the light post 58 distal from the eyepiece through which the illuminating light is supplied to the endoscope 22 is depicted. The illuminating light for the endoscope 22 is supplied by a light source 122 through fiber optic cable 124. The light transmitted by the cable 124 is supplied to the endoscope 22 through an adapter 126 fitted over light post 58.

Cable 124 of this version of the invention, as seen by reference to FIGS. 4 and 12, includes elongated core 50 (FIG. 4) of optically transmissive material. The core 50 is covered with insulating tubing 52 that is ideally optically transmissive. In some versions of the invention, tubing 52 is formed out of silicone. Embedded in tubing 52 at diametrically opposed positions are two conductors 62. In one preferred version of the invention, conductors 62 are 26-gauge insulated wire. A light end plug 130 forms a proximal end of the cable 124; this plug is coupled to light source 122. A scope end plug 132 forms the opposed distal end of cable 124. Scope end plug 132 is the portion of the cable 124 that is plugged into adapter 126.

Figure 13:
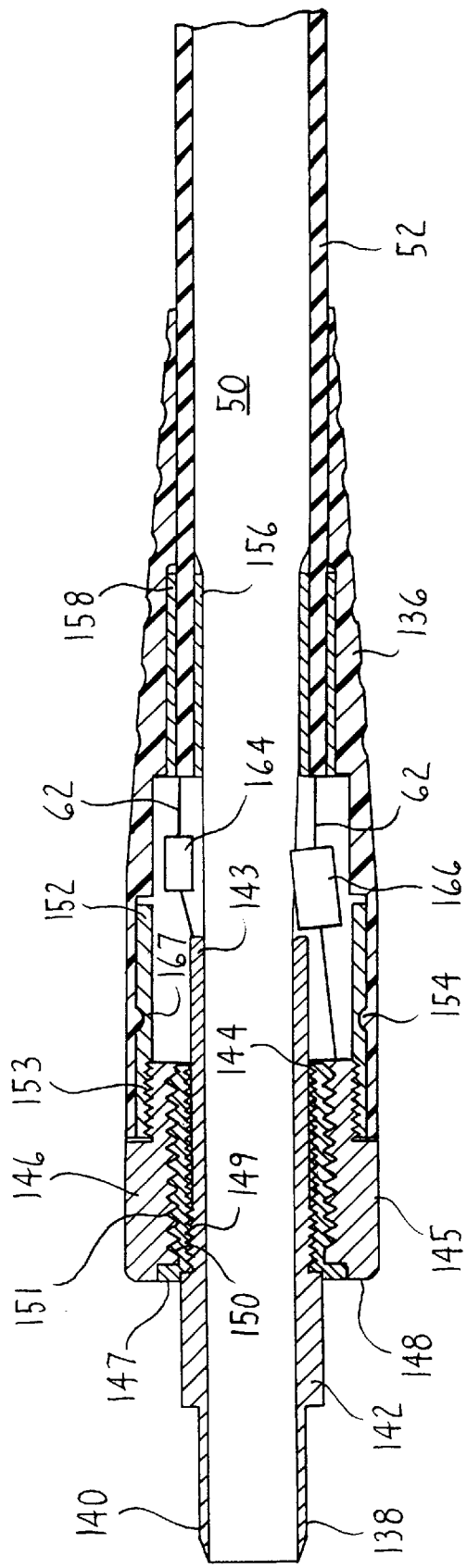
FIG. 13 is a cross-sectional view of the light source plug of the cable of FIG. 12.
Figure 15:
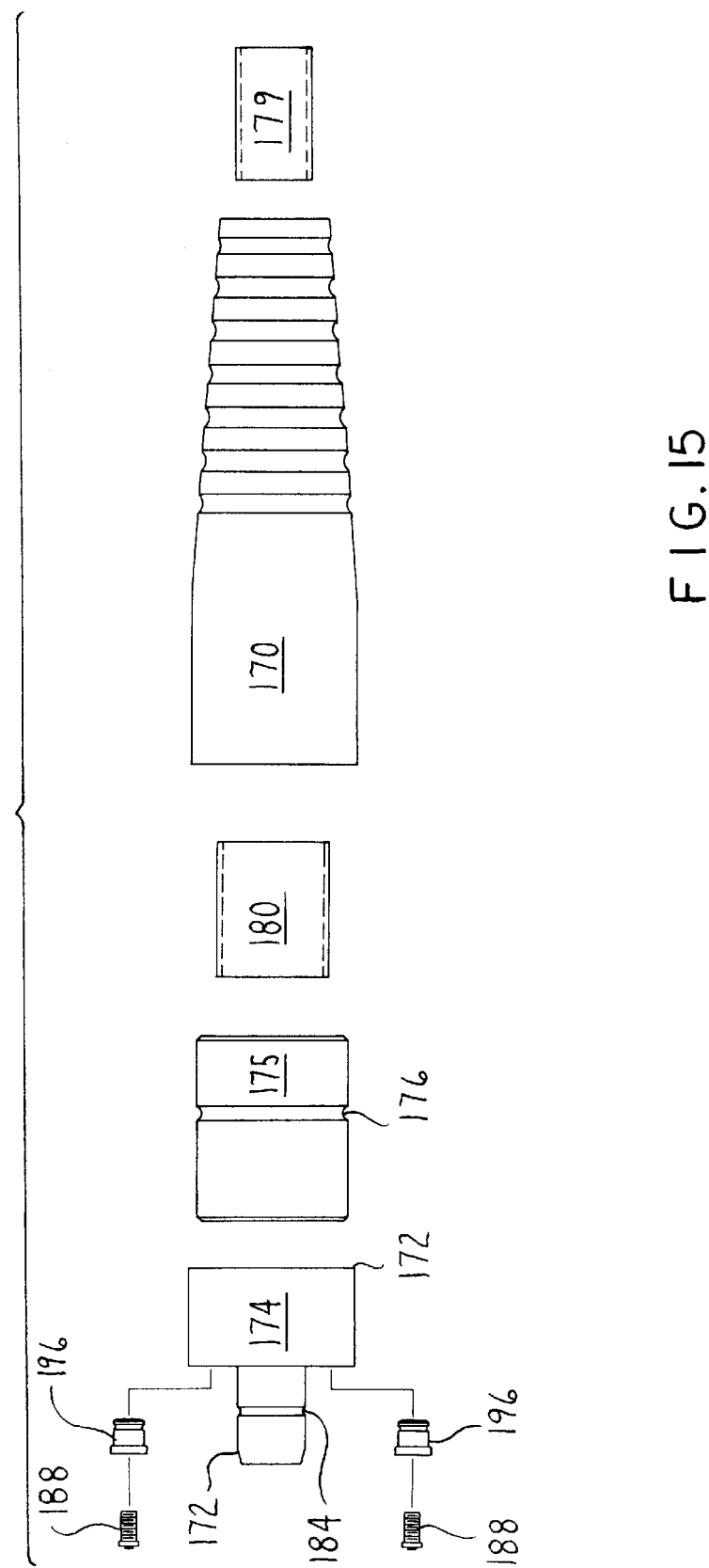
FIG. 15 is an exploded view of the components forming the scope-end plug of the cable of FIG. 12.

Light end plug 130, now described by reference to FIGS. 12 and 13, includes handle 136 formed from silicone that is fitted around the end of insulating tubing 52. The handle 136 is the portion of the light end plug 130 a person grasps to insert/remove the plug from light source 122. A light input tip 138 formed of stainless steel or other electrically conductive material is seated in the handle 136 and extends forwardly therefrom. The light input tip 138 is the mechanical component of plug 130 that covers the portion of the core 50 that extends forward of the handle, the portion that is seated inside the light source 122. Light input tip 138 is more specifically formed to have a stem section 140, that functions as the most forward extending portion of the cable.

Immediately distal to stem section 140, light input tip 138 is formed with an intermediate section 142 that has an outer diameter greater than that of the stem section. Light input tip 138 is also formed with a tail section 143. Tail section 143 has an outer diameter slightly greater than that of stem section 140 and less than that of intermediate section 142. As will be described hereinafter, the tail section 143 of light input tip 138 extends approximately two-thirds the distance through handle 136. It will be further observed that the portion of tail section 143 adjacent intermediate section 142 is formed with threading 144 for a purpose to be discussed hereinafter.

A cap 145, also formed of stainless steel other conductive material, is located adjacent the open end of handle 136 so as to extend around light input tip 138. The light input tip 138 and the cap 145 are electrically insulated from each other by a sleeve 147 formed from an electrically non-conductive material, typically a plastic able to withstand the high heat and humidity of surgical sterilization (temperature, approximately 270° F., humidity approximately 100%). It is believed that the sleeve can be formed out of an acetal resin plastic sold under the trademark DELRIN.

The cap 145 itself is shaped to have a sleeve-shaped main body 146 that extends circumferentially around the outer surface of sleeve 147. Main body 146 is shaped to define a flat circular face 148 that extends in a plane perpendicular to the longitudinal axis of the cap 145. The face 148 of the cap 145 is the most proximal positioned surface of the cap. It will further be understood that cap 145 is shaped so that face 148 has an inner diameter of approximately 0.560 inches and an outer diameter of approximately 0.750 inches. The significance of these dimensions shall become apparent in the following discussion of how cable 124 is coupled to light source 122.

The inner surface of sleeve 147 is provided with threading 149 that engages light input tip threading 144 for holding the sleeve to the light input tip 138. The inner surface of the cap main body 146 and the outer sleeve 147 are provided with complementary threading 150 and 151, respectively, to facilitate the securement of the cap 145 to the sleeve.

A ferrule 152 is threadedly secured to an inwardly stepped distal portion 153 of cap main body 146. Handle 136 is compression fitted around ferrule 152. To facilitate that coupling of the ferrule 152 and the handle 136, the outer surface of the ferrule is formed with a groove 167 in which a complementary semi-circular profile annular flange 154 integral with the handle 136 is seated. It will further be observed that inside the handle adjacent the end of tubing 52 there is first inner sleeve 156 between the core 50 and the tubing. A second, outer sleeve 158 is located between the tubing 52 and the adjacent surface of the handle 136. Sleeves 156 and 158 are formed of plastic to provide reinforcing strength around the end of the tubing 52.

Scope end plug 132, as seen by reference to FIGS. 12, 14, 14A and 15, includes its own silicone handle 170 that serves as a handgrip for the plug. The scope end plug is further provided with scope end tip 172 formed of stainless steel that is partially seated in handle 170 and extend distally therefrom. More particularly, scope end tip 172 has a relatively wide diameter base section 174 that is seated around the open end of handle 170. Extending distally from base section 174, scope end tip 172 has a stem section 176 in that extends distally out of the handle 170. Fiber optic core 50 is fitted inside stem section 176.

A ferrule 175 is threading secured to an inner wall of scope end tip base section 174 so as to extend proximally, therefrom (towards light source 122). Ferrule 175 is compression fitted into handle 170. To facilitate the securement of the ferrule 175 to the handle 170, the ferrule is provided with an annular groove 176 around the outer surface thereof. Handle 170 is provided with a flange 178 around its inner surface that seats in groove 176. A groove 184 is formed around the outer surface of stem section 176.

It will further be observed that inside scope-end plug 132 an inner sleeve 179 is located between the end of tubing 52 and core 50. An outer sleeve 180 is located between the tubing 52 and the handle 170. Sleeves 179 and 180 are formed from plastic.

Seated inside the base section 174 of scope end tip 172 there are two diametrically opposed contacts 188 formed from stainless steel or other conductive material. Each contact 188 has a solid, cylindrical base 192 as well as a reduced diameter solid boss 194. The bosses 194 extend away from base 192 so as to project distally away from the adjacent surface of the scope end tip base section 174.

Contacts 188 are seated in diametrically opposed holes 190 formed in the base section 174 of scope end tip 172. More particularly, each contact is seated in a sleeve-like insulator 196 that is secured in one of the holes 190. Pilot bores 198 that extend coaxially from holes 190 base section 174 serve as conduits through which conductors 62 are routed to the contacts 188.

FIG. 23 is a schematic drawing illustrating the conductors 62 and other electrically conducting components integral with light cable 124. A resistor 164 is connected between the light input tip 138 and cap 145. (Light input tip 138, cap 145 and contacts 188 are represented as terminals in FIG. 23.) A resistor 166 extends from the junction of cap 145 and resistor 164. One of the conductors 62 is series connected between the free end of resistor 166 and one of the contacts 188. A second of the conductors 62 extends from the junction of resistor 164 and light input tip 138 to the second of the contacts 188. In some versions of the invention, resistors 164 and 166 have resistances of between 10K and 1 MEG Ω and are approximately equal in resistance. In still more preferred versions of the invention, resistors 164 and 166 have a resistance between approximately 100K and 220K Ω.

Physically, resistors 164 and 166 are disposed in a void space within light end plug handle 136. Silicone potting material is used to fill the space around resistors 164 and 166 to provide form to the plug 130.

Figure 16:
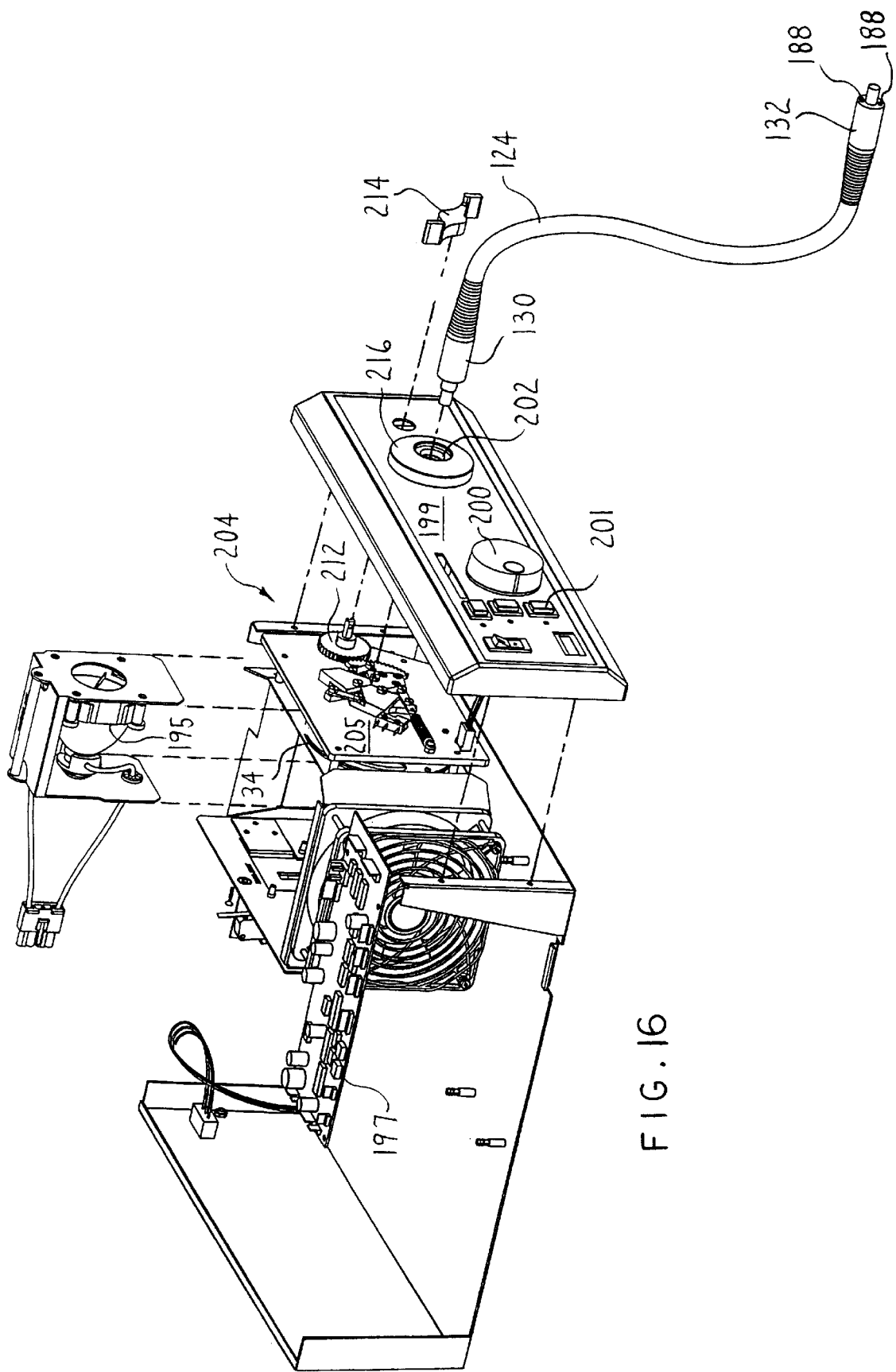
FIG. 16 is an exploded view of the alternative light source.

Light source 122, now described by reference to FIGS. 11, 16 and 17 includes a lamp 195 for emitting the light used to illuminate the surgical site. The intensity of the light emitted by lamp 195 is controlled by the previously described adjustably positionable shutter 34. Also integral with the light source is an intensity control circuit 197 for controlling the actuation of the motor 37 (FIG. 2) that controls the position of the shutter 34.

The brightness of light emitted by light source 122 is manually set by actuation of a intensity control knob 200 disposed outside of a face plate 199 of the light source. Light source 122 is manually placed in/removed from the standby state by the depression of a control switch 201 also on the face plate 199. The placement of the light source in the standby state results in the actuation of the motor 37 so as to cause shutter 34 to be placed in the position wherein only a minimal amount of light is emitted from the light source.

The light end plug 130 of cable 124 is releasably secured in a socket 202 of the light source 122. Socket 202 includes a clamp assembly 204 mounted to a jaw plate 205 located immediately rearward of face plate 199. Clamp assembly 204 includes three jaws 206 that are pivotally mounted to jaw plate 205. Each jaw 206 is formed from a conductive metal such as aluminum and is shaped to have two flat surfaces, not identified. When clamp assembly 204 is in the fully closed state, the flat surfaces of the jaws 206 abut each other. The opening of the clamp assembly 204 causes the jaws 206 to move apart from each other. The jaws 206 are interconnected together for synchronous motion by a jaw gear 208 and a set of arms 210. A spring 211 connected between jaw plate 205 and one of the arms 210 urges the clamp assembly 204 towards the closed state.

The open/closed state of the clamp assembly 204 is controlled by a hub gear 212 rotatably secured to jaw plate 205 that engages jaw gear 208. The hub gear 212 is manually rotated by a release knob 214 mounted outside of the light source face plate 199. When a cable 122 is inserted in the socket 202, release knob 214 is rotated to spread the jaws 206 apart. After the light end plug 130 of the cable 122 is inserted in the socket 202, knob 214 is rotated to open the jaws 206 so that they can be then clamped around the stem of the light input tip 138.

A microswitch 213 is mounted to jaw plate 205 so as to be adjacent one of the jaws 206. The open/closed state of microswitch 213 is controlled by the open/closed state of clamp assembly 204. When the clamp assembly 204 is closed, the adjacent jaw 206 is spaced from the wiper of the microswitch, wiper not illustrated, and the microswitch is in the open state. Once the clamp assembly 204 is opened to accommodate a light cable, the jaw 206 adjacent microswitch 213 abuts the wiper so as to close the microswitch. In some preferred embodiments of the invention, microswitch 213 is positioned so that it closes upon the clamp assembly 204 being opened enough to hold a cable with a tip at least 0.125 inches in diameter, the smallest diameter for a conventional light cable.

It will further be observed that there is a wire 215 that extends from one of the jaws 206. Wire 215 is connected to the jaw 206 to the intensity control circuit 197. Thus, when a jaw abuts the metal of the light input tip 138, the tip is connected to the intensity control circuit 197.

Socket 202 also includes a knob assembly 216, seen best in FIGS. 18 and 19, that is secured to the face plate 199 of the light source through which the light input tip 138 extends. Knob assembly 216 includes a circular insert 218 that is secured to the outer surface of face plate 199. Insert 218 is formed from non-conductive material such as DELRIN. Insert 218 is shaped to have a center opening 220 through which the light input tip 138 extends. There is also a large, outwardly directed counterbore 222 around center opening 220. The surface of the insert that defines the base of counterbore 222 is formed with a groove 224.

A contact ring 228 formed of brass or other electrically conductive material, is seated in the counterbore 222 of insert 218. It will be noted that in the depicted version of the invention, the surface of the contact ring 228 that faces inwardly is formed with a groove 230. It will be further understood that contact ring 228 is shaped to have a center opening 231 with a diameter of between approximately 0.650 and 0.750 inches. The contact ring 228 is so dimensioned so that a conventional cable, a cable that does not have scope-sensing circuitry, can be secured in socket 202 without physically contacting ring 228. Most conventional cables light-transmitting cables are provided with light end plugs that have outer diameters less than the diameter of opening 231 of contact ring 228.

Ring 228 is held in place by a non-conductive knob 232 that is compression secured over insert 218. Knob 232 is formed with an opening 234 to allow the scope end plug 130 to be inserted therein. Nevertheless, it will be noted that the portion of the knob 232 that defines opening 234 subtends the outer perimeter of contact ring 228 to hold the ring in position.

Contact ring 228 is outwardly biased by a spring 236 located between the ring and insert 218. The turns of the spring 236 located at the opposed ends thereof are located in grooves 224 and 230 of, respectively, the insert 218 and the contact ring 228. An electrical connection between the intensity control circuit 197 and conductive ring 228 by a conductor 238. Insert 218 is provided with a through hole 240 to allow conductor 238 to extend therethrough. Conductive ring 228 is provided with a bore 242 to facilitate the securement of the conductor 238 to the ring.

Figure 20:
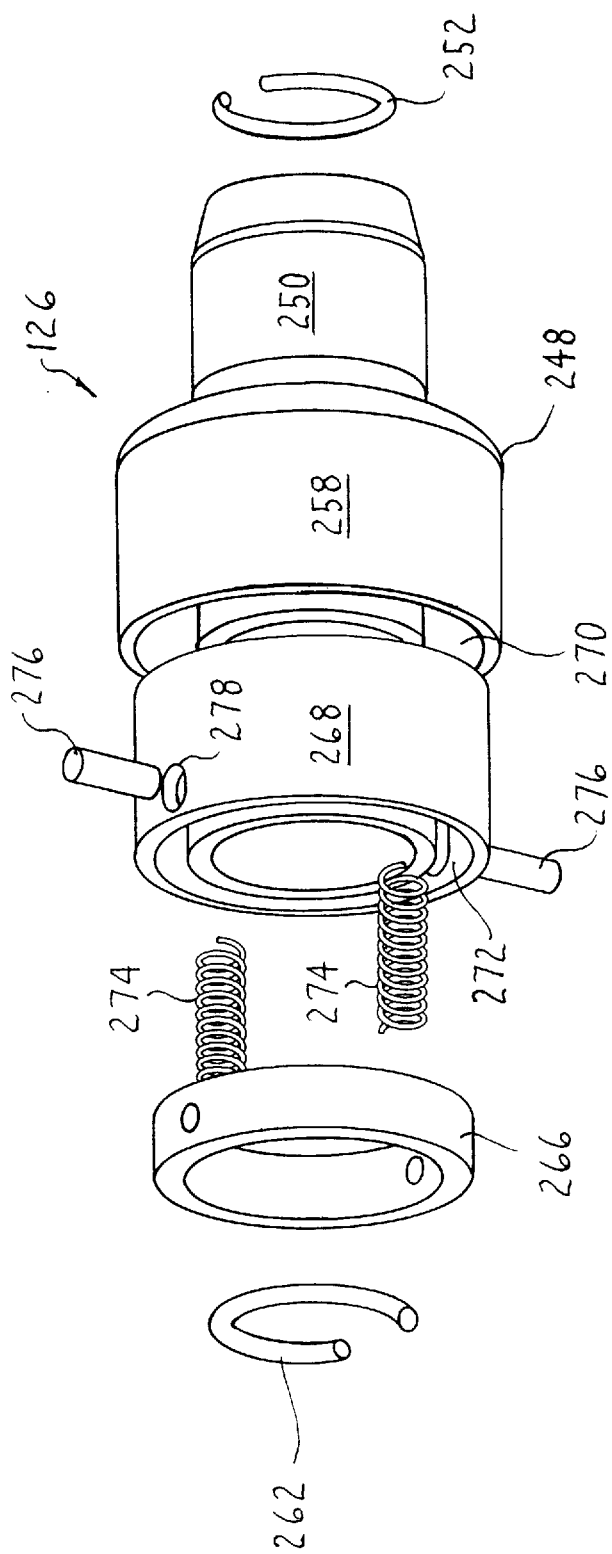
FIG. 20 is an exploded view of the components forming the adaptor fitted to the endoscope.

The adapter 126 to which the scope end plug 132 is secured is now described by reference to reference to FIGS. 20, and 21. Adapter 126 includes a body shell 248 formed of metal that has a scope end 250 fitted over the light post 58 of the endoscope 22. Scope end 250 is formed to define a scope bore 251 having a diameter that is a function of the outer diameter of the complementary light post 58. A split-O-ring snap ring 252 is fitted in a groove 254 formed around the inner wall of the body shell 248 that defines scope bore 251. When the adapter 126 is fitted over light post 58, snap ring 252 seats in a complementary groove 253 (FIG. 11) around the outer diameter of the light post 58 to hold the adapter to the light post.

Body shell 248 is further formed to have a plug end 258 with a diameter greater than that of the scope end 250. Plug end 258 has a plug bore 260 coaxial with and in direct communication with scope bore 251. Plug bore 260 is dimensioned to accommodate the scope end tip 172 of scope end plug 132. A split-O-ring snap ring 262 is seated in groove 264 formed in the inner wall of body shell 248 that defines plug bore 260. When the scope end plug 132 is coupled to the adapter 126, snap ring 262 seats in groove 184 formed in the stem section 176 of scope end tip 172.

Adapter 126 further includes a circular contact ring 266 for establishing a short circuit between contacts 188. Contact ring 266 is seated in insulator 268 that is disposed in the proximal end of body shell 248. More particularly, the open face of plug end 258 of body shell 248 is formed with an annular channel 270 in which the sleeve-like insulator 268 is threadedly secured or press fitted. Insulator 268 is formed from a non-conductive, sterilizable plastic such as is sold under the trademark ULTEM.

The outer, proximal, face of the insulator 268 is shaped to have a groove 272 in which contact ring 266 is seated. Contact ring 266 is outwardly biased towards the scope end plug 132 by a pair of springs 274 seated in groove 272 of insulator 268. Outward movement of contact ring 266 is limited by two opposed pins 276 also formed from ULTEM plastic. Pins 276 extend through openings 278 formed in the outer wall of insulator 268 and through bores 280 formed in contact ring 266. It will be observed that opening 278 of the insulator 268 have an oval profile so as to allow the longitudinal movement of contact ring 266 relative to the insulator. In the absence of any opposing force, the springs 274 bias the contact ring 266 so it projects a slight distance away from the insulator 268.

Figure 22A:
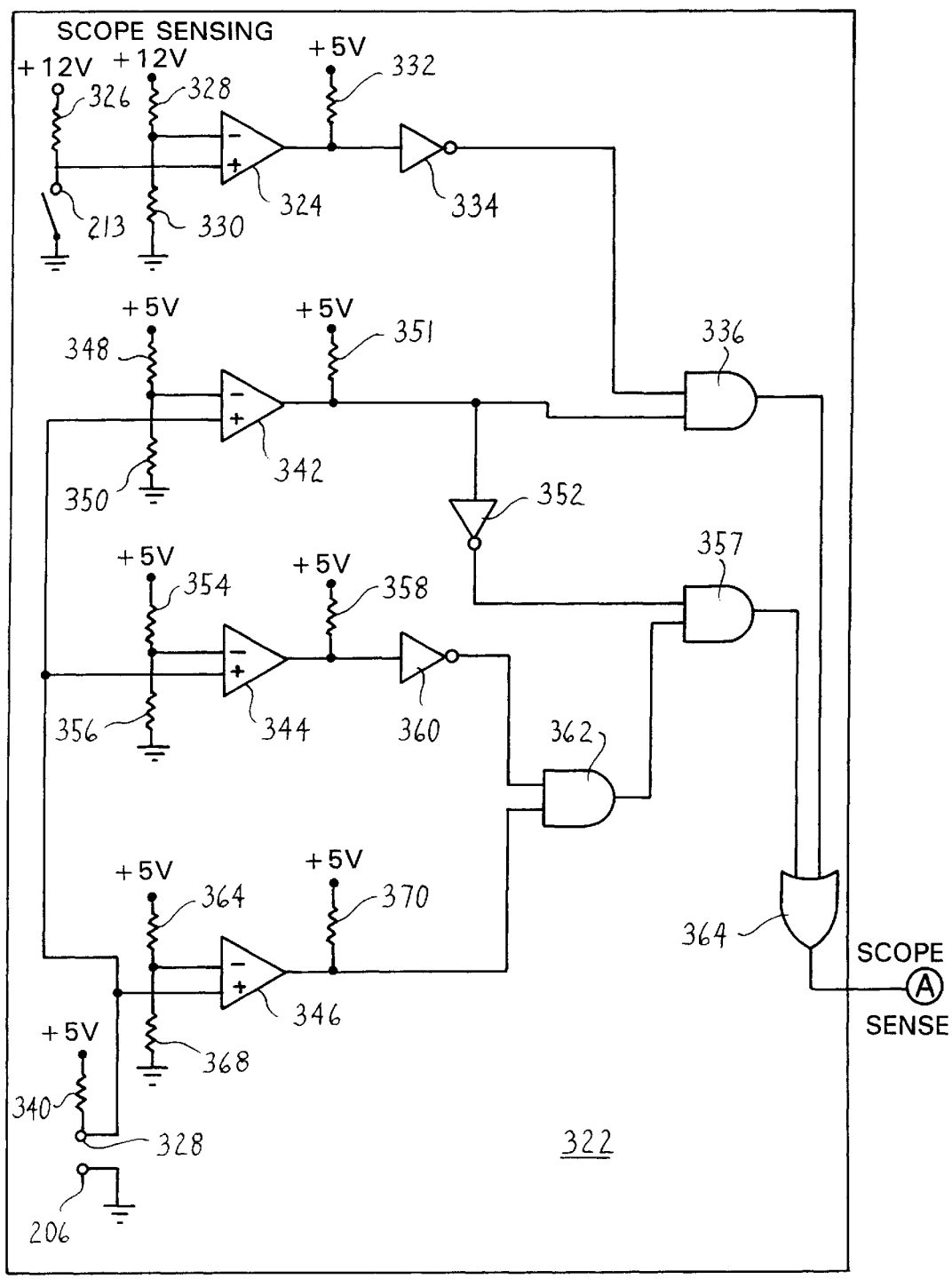
FIGS. 22A and 22B are arranged together to form a schematic and block diagram of the intensity control circuit 197 internal to the light source.
Figure 22B:
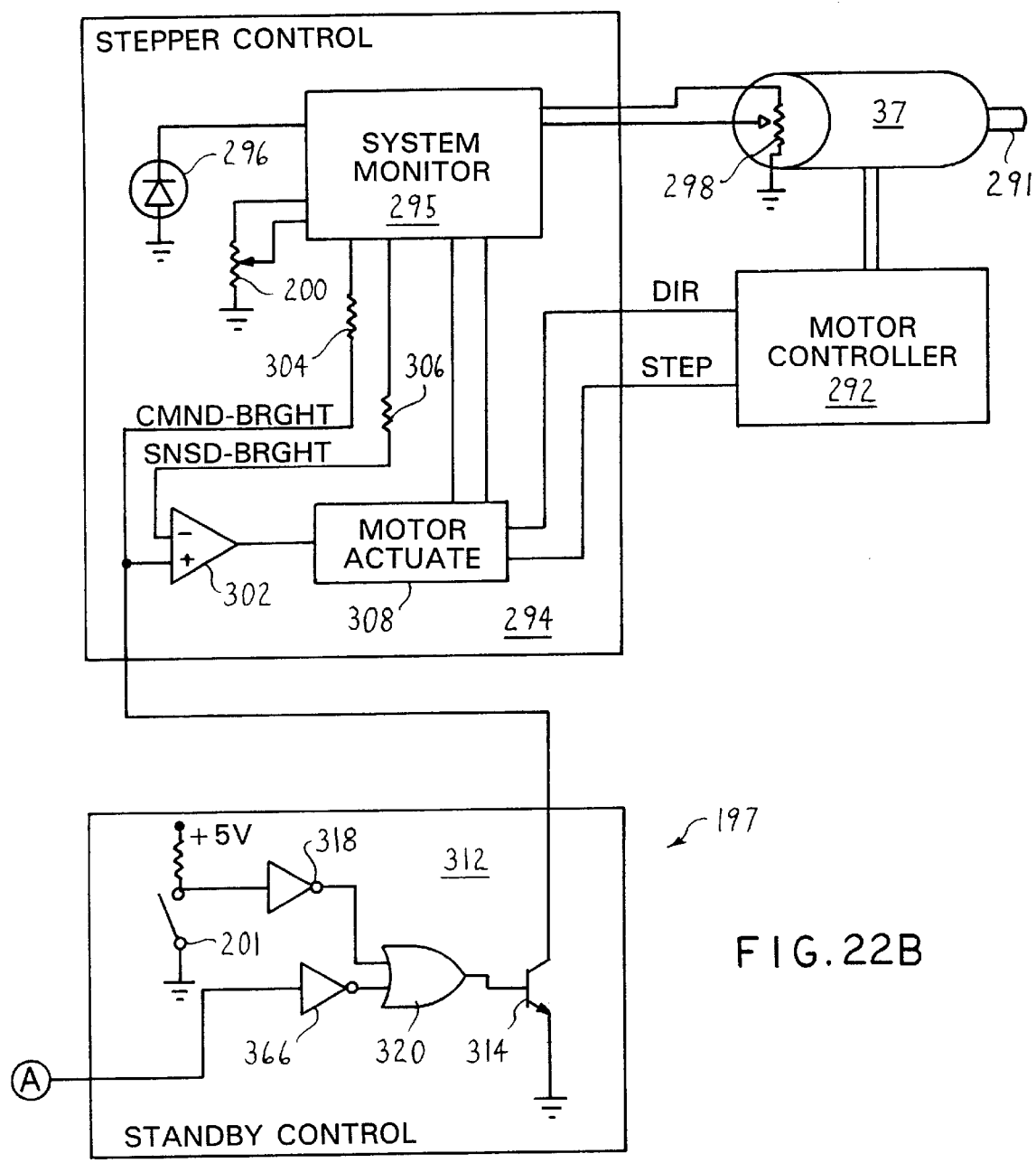

The intensity control circuit 197 internal to light source 122 that controls the actuation of stepper motor 37 is now described by reference to FIGS. 22A and 22B. Intensity control circuit includes a motor controller 292 that actually applies controls the application of commutation currents to the internal windings of motor 37 so as to cause the desired displacement of the motor rotor 291 and shutter 34 (FIG. 2) connected thereto. Integral with many motor controllers 292 is an actual motor controller chip, (not illustrated,) that actually ties the motor windings to voltage source and ground so as to cause current flow through the windings. In some preferred versions of the invention, a UC3517 motor controller integrated circuit chip manufactured by Unitrode is employed in motor controller 292.

Motor controller 292 actuates the motor based on signals received by a stepper control 294. More particularly, stepper control 294 provides motor controller 292 with DIRECTION (DIR) and STEP signals. The DIRECTION signal provides an indication if current is to be applied to the motor 37 to cause rotor 291 movement in either the clockwise or counterclockwise direction. The STEP signal is the actual signal that is asserted to provide an indication that the motor is to be actuated.

When the light source 122 is not in the standby mode, stepper control 294 regulates motor actuation based on signals produced by a system monitor 295. The system monitor 295 monitors signals, other than those related to the standby mode, that are produced by the light source 122. In particular, system monitor 295 monitors the signal produced by the user actuation of intensity control knob 200, herein represented as potentiometer. System monitor 295 also receives a luminosity signal representative of the light present at the surgical site. The signal is received from a photosensitive transducer, represented by photosensitive diode 296, integral with the video camera that receives the light transmitted from the surgical site through endoscope 22. The system monitor 295 is also tied to a sensor integral with motor 37, sensor representative by potentiometer 298, that provides a signal representative of the rotation of the motor rotor 291.

Based on the received input signals, system monitor produces two output signals, a COMMAND BRIGHTNESS (CMND-BRGHT) signal and a SENSED-BRIGHTNESS signal (SNSD-BRGHT) signal. The COMMAND-BRIGHTNESS signal is representative of the user-desired intensity of the light that should be emitted by the light source. The SENSED-BRIGHTNESS signal is representative of the measured brightness. Both BRIGHTNESS signals are adjusted in real-time based on the feedback signals received from the motor 37, intensity control knob 200 and the photosensitive transducer 296.

The COMMAND-BRIGHTNESS and SENSED-BRIGHTNESS signals are applied, respectively to the non-inverting and inverting inputs of a master comparator 302 also integral with stepper control 294. More particularly, it will be noted that the COMMAND-BRIGHTNESS signal is applied to master comparator 302 through a resistor 304 and the SENSED-BRIGHTNESS signal is applied through a resistor 306. The output signal produced by master comparator 302 is applied to a motor actuate circuit 308. The motor actuate circuit 308 also receives certain supplemental control signals produced by the system monitor 295. Based on the signals it receives, motor actuate circuit 308, in turn, selectively asserts the DIRECTION and STEP signals to the motor controller 292 so as to cause the actuation of the motor 37.

Intensity control circuit 197 also includes a standby control circuit 312. Standby control circuit 312 is connected to stepper control circuit 294 for causing the actuation of the motor so as result in the shutter 34 being set to its minimal-light-out position regardless of the states of the COMMAND- and SENSED-BRIGHTNESS signals. In the illustrated version of the invention, standby control circuit 312 includes an NPN transistor 314 with a collector tied to the noninverting input of master comparator 302 and an emitter tied to ground. When transistor 314 is turned on, the noninverting input of master comparator 302 is tied to ground. The application of this "zero" voltage signal to comparator 302 causes the comparator to assert a signal that in turn causes motor actuate circuit 308 to assert DIRECTION and STEP signals that result in the actuation of the motor 37 so that shutter 34 is rotated to the minimal-light-out state.

A voltage is applied to the base of transistor 314 to turn the transistor on through one of two sources. First, the light source can be manually placed in the standby mode by the closing of control switch 201. This pulls the voltage presented to the input of invertor 318 low so as to cause the invertor to assert a high voltage, a transistor on voltage, to transistor 314 through OR gate 320. Normally, when switch 201 is open, a high voltage is presented to the input of invertor 318 through a resistor 321.

Alternatively, a transistor-on voltage is applied to transistor 314 from a scope-sensing circuit 322. Scope-sensing circuit 322 monitors signals representative of whether or not a cable is plugged into the light source 122, the type of cable and, if it is a scope-sensing cable, whether or not an endoscope 22 is attached thereto. Depending on the signals received by the scope-sensing circuit 322, the scope-sensing circuit asserts a SCOPE-SENSED signal to standby control circuit 312. If the SCOPE-SENSED signal is not asserted, transistor 314 is turned on to hold the light source 122 in the standby mode. If the SCOPE-SENSED signal is received, standby control circuit 312 is placed in what is referred to as a "toggle" mode. When the standby control circuit 312 is in the toggle mode, the standby control circuit can then be used to put the light source 122 in and take the light source out of the standby mode by the manual setting of control switch 201.

Scope-sensing circuit 322 includes a comparator 324 that produces a signal indicative of whether or not a cable is clamped to the light source 122. Comparator 324 has a noninverting input that is tied to a +12 VDC voltage source through a pull-up resistor 326. The noninverting input of comparator 324 is also tied to one terminal of microswitch 213. The opposed end of microswitch 213 is tied to ground. The inverting input of comparator 324 is applied to the junction of two series connected resistors 328 and 330 that are tied between the +12 VDC voltage source and ground. Resistors 328 and 330 are selected so as to cause a signal between 1.0 and 11.0 VDC to be applied to the inverting input of comparator 324.

The output of comparator 324 is tied to a +5 VDC voltage source through a resistor 332. The output signal produced by comparator 324 is applied to an invertor 334. The output of invertor 334 is applied to one input of an AND gate 336.

Also integral with scope-sensing circuit 322 are the conductive jaws 206 of clamp assembly 204 and the conductive contact ring 228 of socket 202. (The jaws 226 and contact ring 228 being represented as terminals in FIG. 22A). Wire 215 (FIG. 17) tied to the jaw 206 is connected to ground. Contact ring 228 is tied to the +5 VDC voltage source through a resistor 340. The voltage present at contact ring 228 is thus a function of the type of cable connected to the light source 122 and, if it is a scope-sensing cable 124, whether or not the cable is attached to an endoscope 22.

The voltage present at contact ring 228 is applied to the noninverting inputs of three separate comparators 342, 344, and 346. The inverting input of comparator 342 is tied to the junction of resistors 348 and 350 that form a voltage divider between the +5 VDC voltage source and ground. Resistors 348 and 350 are selected to present a voltage between 3.0 and 4.0 VDC to the inverting input of comparator 342. The +5 VDC voltage source is connected to the output of comparator 342 through a resistor 351. The output signal from comparator 342 is applied to the second input of AND gate 336.

The output signal from comparator 342 is also applied to the input of an invertor 352. The signal produced by invertor 352 is applied to one input of an AND gate 357.

The inverting input of comparator 344 is tied to the junction of two series connected resistors 354 and 356. Resistors 354 and 356 are connected between the +5 VDC voltage source and ground and have the same resistance so as to present a 2.5 VDC signal to the inverting input of comparator 344. The +5 VDC voltage source is tied to the output of comparator 344 through resistor 358. The output signal from comparator 344 is applied to the input of an invertor 360. The signal produced by invertor 360 is applied to one of the inputs of an AND gate 362.

The inverting input of comparator 346 is connected to the junction of two series connected resistors 364 and 368. Resistors 364 and 368 extend between the +5 VDC source and ground and are selected so that the voltage present at the junction thereof is between approximately 1.0 and 1.5 VDC. The +5 VDC voltage source is tied to the output of comparator 346 through a resistor 370. The output signal produced by comparator 346 is applied to the second input of AND gate 362.

The output signal produced by AND gate 362 is applied to the second input of AND gate 357. The output signals produced by AND gates 336 and 357 are applied to the inputs of an OR gate 364. The signal produced by OR gate 364 is the SCOPE-SENSED signal produced by scope-sensing circuit 322. The signal produced by OR gate 364 is applied to standby control circuit 312. More particularly, in the illustrated version of the invention, the signals produced by OR gate 364 is applied to an invertor 366 integral with standby control circuit 312. The output signal from invertor 366 is the second input signal into OR gate 320.

When the light source 122 is actuated and there is no cable attached thereto, microswitch 213 is open and a 5.0 VDC signal is present at the contact ring 228. Owing to the state of microswitch 213, comparator 324 presents a +5 VDC high signal to invertor 334. Invertor 334 thus produces a low signal to its complementary input into AND gate 336. The AND gate 336 thus asserts a low signal to one of the inputs of OR gate 364.

Owing to the presence of the +5 VDC signal at contact ring 228, comparator 342 likewise asserts a high signal. This high signal is inverted by invertor 352. The low signal produced by invertor 352 causes AND gate 357 to likewise produce a low signal. Thus, two low signals are provided to OR gate 364. The OR gate 364 thus asserts a low signal which is interpreted by standby control circuit 312 as a SCOPE-SENSED signal, an instruction to place the light source in the standby mode. In the depicted version of the invention, this signal is inverted by invertor 366. The resultant high signal is thus applied through OR gate 320 to the base of transistor 314 to turn the transistor on.

Figure 17:
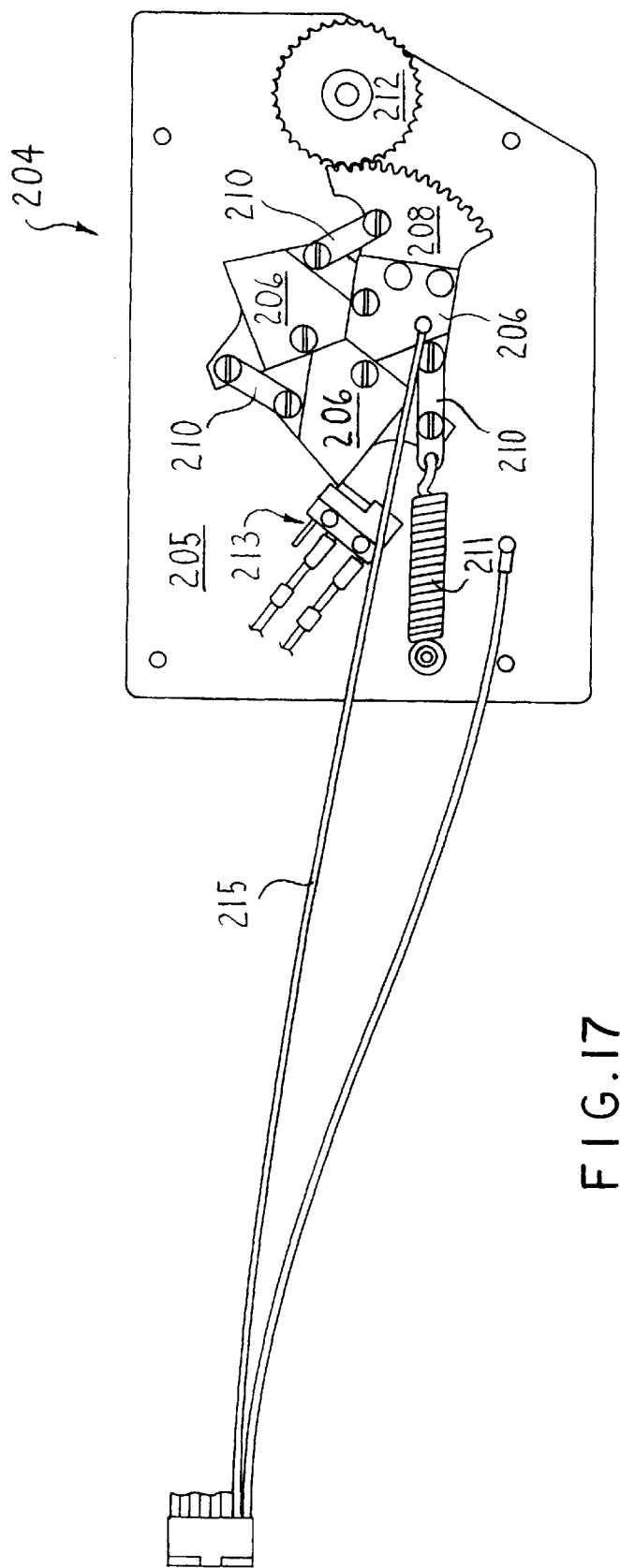
FIG. 17 depicts the clamping mechanism integral with the light source used to secure the cable thereto.

When a light cable, regardless of its scope-sensing capabilities, is secured in socket 202, microswitch 213 is closed by the outward movement of the adjacent jaw 206 (FIG. 17). The closing of microswitch 213 causes the voltage presented to the noninverting input of comparator 324 falls to zero and the output of the comparator likewise goes low. Owing to the inversion of the signal produced by comparator 324 by invertor 334, a high signal is thus presented to one input of AND gate 336.

If a conventional cable is attached to the light source 122, the cap integral with the light end plug will be spaced a slight distance inwardly from the contact ring 228. Thus, the circuit between conductive jaws 206 and contact ring 228 remains open. Consequently, the signals produced by comparators 342, 344 and 346 are the same as they were in the no-cable state. Therefore, comparator 342 produces a high signal that is presented to the second input of AND gate 336. Since both inputs to AND gate 336 are high, the AND gate produces a high signal to OR gate 364. The OR gate 364 thus asserts a high, SCOPE-SENSED signal to standby control circuit 312.

Invertor 366 inverts the SCOPE-SENSED signal and applies it to OR gate 320. Thus, the standby control circuit 312 does not automatically place the light source in the standby mode. Switch 201 can, however, be actuated to manually place the light source in and remove the light source from the standby mode.

If a scope-sensing cable 124 is coupled to the light source 122, a first electrical connection is established between jaw 206 and light input tip 138 as seen by reference to FIG. 23. Simultaneously, a second electrical connection is established between cap 145 and contact ring 228. Thus, the electrical circuit between jaw 206 and contact ring 228 is closed. Assuming the cable 124 is not attached to an endoscope 22, only resistor 164 is placed in this circuit. Consequently, the voltage present at contact ring 228 drops to approximately 2.8 VDC.

When the above no-scope voltage is presented to comparator 342, the output signal of the comparator transitions low. The low signal produced by comparator 342 causes the output signal produced by AND gates 336 to likewise transition low. The low signal produced by AND gate 336 is applied to one input of OR gate 364. When the contact ring 228 voltage is in this no-scope voltage state, comparator 344 will continue to assert a high state signal. This signal is inverted low by invertor 360. The low signal produced by invertor 360 is applied to one input of AND gate 362 so as to place the output signal from AND gate 362 in the low state.

The low state of AND gate 362 causes a like transition of AND gate 357. Consequently, two low signals are applied to OR gate 364. The OR gate 364 thus asserts a low SCOPE-SENSED signal to standby control circuit 312. The receipt of the SCOPE-SENSED signal, as discussed, turns on transistor 314 so as to force the light source 122 into the standby mode.

If the scope-sensing cable 124 is connected to an endoscope 22 to which an adapter 126 is attached, the cable contacts 188 abut adapter contact ring 266. Thus, contact ring 266 completes the connection between conductors 62 so as to place resistor 166 in parallel with resistor 164. The insertion of resistor 166 into the circuit thus serves to cause the voltage present at light source contact ring 228 to fall to approximately 2.0 VDC.

When the contact ring 228 voltage drops to 2.0 VDC, the scope-connected voltage, comparator 342 will continue to assert a low output signal. It will be observed, however, that the output signal from comparator 342 is inverted by invertor 352 and the resultant high signal is applied to one of the inputs of AND gate 357.

The drop of contact ring 228 voltage to the scope-connected level does however cause the output signal from comparator 344 to transition low. This low output signal is inverted by invertor 360 and applied as a high signal to one input of AND gate 362. The second input of AND gate 362 is, in this state, receiving a high signal from comparator 346. Consequently, AND gate 362 asserts a high signal to the second input of AND gate 357.

Since, in the scope-connected state, AND gate 357 receives as inputs two high signals, the AND gate asserts a high signal. This high signal is applied through OR gate 364 to the standby control circuit as the SCOPE-SENSED signal. The receipt of the SCOPE-SENSED signal cause the standby control circuit to turn off transistor 314 so that system monitor circuit 295 provides the signals employed for controlling the intensity of the light emitted by light source 122. Light source 132 can still manually be placed in the standby mode by the closing of switch 201.

An advantage of endoscope system 120 is that light source 122 can be used with both the scope-sensing cable 124 and with conventional cables. When a conventional cable is plugged into the light source 122, the light source operates in a conventional manner and can be placed in the standby mode by depression of control button 201. When the scope-sensing cable 124 is employed, intensity control circuit 197 will automatically place the light source in the standby mode whenever the cable is not connected to the scope adapter 126.

It should be recognized that the foregoing description is directed to one specific embodiment of the invention and that other versions of the invention may vary from what has been described. Other versions of the invention may employ cable plugs, light source sockets and endoscope cable adapters different from what has been described. For example, in some versions of the invention, the conductive contacts on the cable plugs and complementary sockets/adapters may not be longitudinally spaced apart from each other as has been described. In these versions of the invention, these contacts may be located at different radial locations around a common circumference.

Still other versions of the invention may not have the open conductors of the described embodiment. In some versions of the invention, a small switch may be located in the scope end plug of the fiber optic cable. This switch is provided with a contact that only closes the connection across conductors 62 when a complementary moving member is displaced upon the coupling of the cable to the endoscope 22.

Moreover, it should be recognized that the intensity control circuit 197 may be provided with override switches that allow surgical personnel to regulate the emission of light independently of the connected/disconnected state of the associated fiber optic, scope-sensing light cable. It should similarly be recognized that the mechanism for controlling the intensity of the light emitted by the light source may also vary from what has been described. For example, other versions of the invention may not employ the shutter with variable aperture. In these versions of the invention, the intensity control circuit may regulate the energization voltage or current applied to the light emitting bulb in order to regulate the amount of light emitted by the bulb itself. Also, the intensity controller could be configured to turn the bulb or other light emitting element off if the cable is disconnected from the complementary endoscope.

Also, while the disclosed circuit 197 is shown as comprising a set of discrete components, that need not always be the case. In some versions of the invention, the intensity control circuit may include a microprocessor, specifically programmed to respond to conventional cable/scope-sensing cable and scope connected/scope disconnect signal states by placing the light source in and out of the standby mode. In these, as well as in other versions of the invention, the circuitry internal to the scope-sensing cable may be different from what has been described. For example, it may be desirable to remove the resistors and substitute therefor logic components capable of withstand the sterilization environment to which the cable is exposed. Furthermore, in some versions of the invention, it may be desirable to provide two pairs of conductors in the fiber optical cable. A first one of the pairs may be connected to the adapter 126 as described. The second pair of conductors would actually be a single conductor that is connected to two additional contacts integral with the proximal-end plug. The scope-sensing circuit could then monitor whether or not complementary conductors associated with the light source socket form either and open or closed circuit. Based on the state of this circuit, the scope-sensing circuit internal to the light source could evaluate the conventional cable/scope-sensing cable and scope connected/disconnected states of the system 120. This circuit would eliminate the need to provide the scope-sensing cable with resistors or other discrete components.

It should further be recognized that the contact ring 266 may be integrally installed on the light post 58 of the endoscope 22.

Therefore, it is the object of the appended claims to cover all such modifications as common within the true spirit and scope of this invention.

The embodiments of the invention in which an exclusive property or privilege is claimed are defined as follows:

1. A light source for providing light to an endoscope over a fiber optic cable, said light source including:
   a light emitting element;
   a socket for receiving a fiber optical cable that is connectable to the endoscope, said socket being positioned so that when the fiber optic cable is inserted in said socket, light emitted by said light emitting element is transmitted through the fiber optic cable;
   a light intensity controller connected to said light emitting element for regulating the amount of light emitted by said light emitting element through said socket, wherein said light intensity controller is configured to selectively place said light emitting element in a standby mode in which said light-emitting element emits a reduced amount of light; and
   a scope detector circuit connected to said socket for determining if the fiber optic cable is connected/disconnected to said socket, the type of fiber optic cable and if the fiber optic cable is connected to the endoscope, said scope detector also being connected to said light intensity controller to force said light intensity controller to place said light emitting element in the standby mode, wherein:
      when said scope detector circuit determines that no fiber optic cable is attached to said socket, said scope detector circuit forces said light intensity controller to place said light emitting element in the standby mode;
      when said scope detector circuit determines that a first type of fiber optic cable is attached to said socket, said scope detector circuit causes said light intensity controller to release said light emitting element from the standby mode regardless of the connected/ disconnected state of the fiber optic cable to the endoscope;
      when said scope detector circuit determines that a second type of fiber optic cable is connected to said socket and the fiber optic cable is disconnected from the endoscope, said scope detector circuit causes said light intensity controller to force said light emitting element to the standby mode; and
      when said scope detector circuit determines that the second type of fiber optic cable is connected to the socket and the fiber optic cable is connected to the endoscope, said scope detector circuit causes said light intensity controller to release said light emitting element from the standby mode.

2. The light source of claim 1, wherein: said scope detector circuit includes two terminals associated with said socket, each said terminal being adapted to contact a separate complementary conductive contact integral with the fiber optic cable and a means for measuring the signal present across said terminals.

3. The light source of claim 2, wherein said scope detector circuit includes means for applying a test voltage to one of said terminals.

4. The light source of claim 2, wherein one of said terminals is a jaw assembly for securing the fiber optic cable to the light source.

5. The light source of claim 2, wherein one of said terminals is an annular member so that electrical contact can be established between said terminal and the complementary conductive contact of the fiber optic cable at a plurality of different points around a center axis of the fiber optic cable.

6. The light source of claim 2, further including a biasing member for forcing at least one of said terminals into contact with the complementary conductive contact of the fiber optic cable.

7. The light source of claim 1, wherein:
   said light intensity controller includes a standby control circuit responsive to a user-set switch for placing said light emitting element in the standby mode; and
   said scope detector circuit is connected to said standby control circuit for causing said standby control circuit to selectively place said light emitting element in the standby mode regardless of the state of the user-set switch.

8. The light source of claim 1, wherein:
   said light emitting element is a light bulb; and
   said light intensity controller includes: a movable shutter with a variable sized aperture in-line with the light emitted by said light bulb; and a motor connected to said shutter for positioning said aperture relative to the light bulb so as to regulate the quantity of light emitted.

9. The light source of claim 1, wherein: said scope detector circuit includes a voltage measuring circuit for measuring a voltage access two conductors integral with the fiber optic cable; and said scope detector circuit regulates said light intensity controller based on the voltage measured by said voltage measuring circuit.

10. A light source for providing light to an endoscope over a fiber optic cable, said light source including:
   a light emitting element;
   a socket for receiving a fiber optical cable that is connectable to the endoscope, said socket being positioned so that when the fiber optic cable is inserted in said socket, light emitted by said light emitting element is transmitted through the fiber optic cable;
   a light intensity controller connected to said light emitting element for regulating the amount of light emitted by said light emitting element through said socket, wherein said light intensity controller is configured to selectively place said light emitting element in a standby mode in which said light emitting element emits a reduced amount of light;

a clamp assembly adjacent said socket for holding the fiber optic cable in said socket, said clamp assembly including a sensor for generating a signal indicating if the fiber optic cable is inserted in said socket;

a scope detector circuit attached to said socket for determining if a first type or a second type of fiber optic cable is inserted in said socket, and, if the second type fiber optic cable is inserted in said socket, it the fiber optic cable is connected to the endoscope, said scope detector circuit being connected to said clamp assembly sensor to receive the signal indicating when a fiber optic cable is inserted in said socket and being connected to said light intensity controller, wherein:

when the signal from said clamp assembly sensor indicates the fiber optic cable is not inserted in said socket, said scope detector circuit forces said light intensity controller to place said light emitting element in the standby mode;

when the signal from said clamp assembly sensor indicates the fiber optic cable is inserted in said socket and said scope detector circuit determines that the cable is a first type fiber optic cable, said scope detector circuit causes said light intensity controller to release said light emitting element from the standby mode regardless of the connected/disconnected state of the fiber optic cable to the endoscope;

when the signal from said clamp assembly sensor indicates the fiber optic cable is inserted in said socket and said scope detector circuit determines that the cable is a second type fiber optic cable and the fiber optic cable is disconnected from the endoscope, said scope detector circuit causes said light intensity controller to force said light emitting element to the standby mode; and when the signal from said clamp assembly sensor indicates the fiber optic cable is inserted in said socket and said scope detector circuit determines that the cable is a second type fiber optic cable and the fiber optic cable is connected to the endoscope, said scope detector circuit causes said light intensity controller to release said light emitting element from the standby mode.

11. The light source of claim 10, wherein: said scope detector circuit includes two terminals associated with said socket, each said terminal being adapted to contact a separate complementary conductive contact integral with the fiber optic cable and a means for measuring the signal present across said terminals.

12. The light source of claim 11, wherein said scope detector circuit includes means for applying a test voltage to one of said terminals.

13. The light source of claim 10, wherein:
said light intensity controller includes a standby control circuit responsive to a user-set switch for placing said light emitting element in the standby mode; and
said scope detector circuit is connected to said standby control circuit for causing said standby control circuit to selectively place said light emitting element in the standby mode regardless of the state of the user-set switch.

14. A light source for providing light to an endoscope over a fiber optic cable, the fiber optic cable having a plug with conductive contacts, said light source including:

a light emitting element;
a socket for receiving the fiber optical cable, said socket being positioned so that when the fiber optic cable is inserted in said socket, light emitted by said light emitting element is transmitted through the fiber optic cable;
a light intensity controller connected to said light emitting element for regulating the amount of light emitted by said light emitting element through said socket;
a clamp assembly adjacent said socket for holding the fiber optic cable in said socket, said clamp assembly including a jaw for securing the plug of the fiber optic cable; and
a scope detector circuit, said scope detector circuit including two terminals for establishing conductive paths with the contacts of the fiber optic cable plug, wherein said jaw of said clamp assembly is one of said terminals, said scope detector circuit being configured to monitor a signal across the contacts of the plug and being connected to said light intensity controller, wherein, based on the signal across the contacts of the plug, said scope detector circuit controls said light intensity control to cause said light emitting element to emit a select amount of light.

15. The light source of claim 14, wherein:
said light intensity controller is configured to place said light emitting element in a standby mode in which said light emitting element emits a reduced amount of light; and
when said scope detector circuit detects a defined signal across the contacts of the plug, said scope detector circuit forces said light intensity controller to place said light emitting element in the standby mode.

16. The light source of claim 15, wherein: said scope detector circuit further includes a sensor connected to said clamp assembly for providing a signal indicating if the fiber optic cable is inserted in said socket; and, if said sensor indicates there is no fiber optic cable in said socket, said scope detector circuit forces said light intensity controller to place said light emitting element in the standby mode.

17. The light source of claim 15, wherein:
said light intensity controller includes a standby control circuit responsive to a user-set switch for placing said light emitting element in the standby mode; and
said scope detector circuit is connected to said standby control circuit for causing said standby control circuit to selectively place said light emitting element in the standby mode and, when a defined signal across the contacts of the fiber optic cable plug is detected, said scope detector circuit causes said standby control circuit to place said light emitting element in the standby mode regardless of the state of the user-set switch.

18. The light source of claim 14, wherein said scope detector circuit includes a voltage measuring circuit that is connected to said terminals for measuring the voltage across the contacts of the fiber optic cable plug.

19. The light source of claim 18, wherein said scope detector circuit includes a voltage source connected to one of said terminals to apply a voltage to the contact of the fiber optic cable plug with which said terminal is associated.

20. The light source of claim 14, wherein said scope detector circuit includes a voltage measuring circuit for measuring voltage across the contacts of the fiber optic cable plug and said scope detector circuit, based on the voltage measurement made by said voltage measuring circuit, controls said light intensity control to cause said light emitting element to emit a select amount of light.

21. The light source of claim 20, wherein:

said light intensity controller is configured to place said light emitting element in a standby mode in which said light emitting element emits a reduced amount of light; and when said voltage measuring circuit measures a select voltage across the contacts of the fiber optic cable plug, said scope detector circuit forces said light intensity controller to place said light emitting element in the standby mode.

22. The light source of claim 14, wherein said clamp assembly includes a plurality of jaws and said jaws collectively function as one of said terminals of said scope detector circuit.

* * * * *